United States Patent
Davis et al.

(10) Patent No.: US 11,268,144 B2
(45) Date of Patent: Mar. 8, 2022

(54) METHODS AND REAGENTS FOR MOLECULAR PROXIMITY DETECTION USING RNA-GUIDED NUCLEIC ACID BINDING PROTEINS

(71) Applicant: Sigma-Aldrich Co. LLC, St. Louis, MO (US)

(72) Inventors: Gregory D. Davis, St. Louis, MO (US); Vikas B. Palhan, St. Louis, MO (US); Carol A. Kreader, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 447 days.

(21) Appl. No.: 15/762,748

(22) PCT Filed: Sep. 23, 2016

(86) PCT No.: PCT/US2016/053386
§ 371 (c)(1),
(2) Date: Mar. 23, 2018

(87) PCT Pub. No.: WO2017/053762
PCT Pub. Date: Mar. 30, 2017

(65) Prior Publication Data
US 2018/0340221 A1  Nov. 29, 2018

Related U.S. Application Data

(60) Provisional application No. 62/232,023, filed on Sep. 24, 2015.

(51) Int. Cl.
| | | |
|---|---|---|
| *C12Q 1/6876* | (2018.01) | |
| *C12N 9/22* | (2006.01) | |
| *C12N 15/11* | (2006.01) | |
| *C07K 16/40* | (2006.01) | |
| *C12Q 1/6827* | (2018.01) | |
| *C12Q 1/6841* | (2018.01) | |
| *C12Q 1/6853* | (2018.01) | |
| *C12Q 1/682* | (2018.01) | |
| *C12Q 1/6804* | (2018.01) | |

(52) U.S. Cl.
CPC ........... *C12Q 1/6876* (2013.01); *C07K 16/40* (2013.01); *C12N 9/22* (2013.01); *C12N 15/11* (2013.01); *C12Q 1/682* (2013.01); *C12Q 1/6804* (2013.01); *C12Q 1/6827* (2013.01); *C12Q 1/6841* (2013.01); *C12Q 1/6853* (2013.01); *C12N 2310/20* (2017.05); *C12N 2800/80* (2013.01)

(58) Field of Classification Search
CPC .... C12Q 1/6804; C12Q 1/6841; C12Q 1/682; C12N 2310/20; C12N 15/11
See application file for complete search history.

(56) References Cited

U.S. PATENT DOCUMENTS

| | | | |
|---|---|---|---|
| 2007/0017847 A1 | 1/2007 | Leifeld | |
| 2014/0170654 A1* | 6/2014 | Landegren | ........... C12Q 1/6816 435/6.11 |
| 2014/0228239 A1 | 8/2014 | McCoy et al. | |
| 2014/0364333 A1* | 12/2014 | Wu | ....... C12Q 1/6841 506/9 |
| 2017/0306306 A1* | 10/2017 | Potter | ................. C12N 15/902 |
| 2018/0250424 A1* | 9/2018 | Cotta-Ramusino | ......................... C12N 15/113 |

FOREIGN PATENT DOCUMENTS

| | | |
|---|---|---|
| JP | 2017-530695 A | 10/2017 |
| WO | 2012/152942 A1 | 11/2012 |
| WO | 2015048690 A1 | 4/2015 |
| WO | 2016/028843 A2 | 2/2016 |
| WO | WO-2016061523 A1 * | 4/2016 ........... C12Q 1/6804 |
| WO | 2017/053762 A1 | 3/2017 |

OTHER PUBLICATIONS

Makarova et al. An updated evolutionary classification of CRISPR-Cas systems. Nature Reviews. Microbiology. Vol. 13, No. 11, pp. 722-736, Sep. 28, 2015. (Year: 2015).*
Nishimasu et al. Crystal structure of Cas9 in complex with guide RNA and target DNA. Cell, vol. 156, pp. 935-949, Feb. 27, 2014. (Year: 2014).*
O'Connell et al. Programmable RNA recognition and cleavage by CRISPR/Cas9, vol. 516, No. 7530, pp. 263-266, Sep. 28, 2014. (Year: 2014).*
Ding et al. Recent advances in genome editing using CRISPR/Cas9. Frontiers in Plant Science, vol. 7, 703, May 24, 2016, printed as pp. 1-12. (Year: 2016).*
Deng, et al., "CASFISH: CRISPR/Cas9-mediated in situ labeling of genomic loci in fixed cells", PNAS, vol. 112, No. 38, Sep. 22, 2015, p. 11870-11875.
Liu et al., "Natural variation in ARF18 gene simultaneously affects seed weight and silique length in polyploid rapeseed", Proceedings of the National Academy of Sciences of the United States of America, 2015, 112(37):E5123-32 DOI:10.1073/pnas.1502160112.
Koos et al., "Proximity-dependent initiation of hybridization chain reaction", Nature Communications, 2015, 6:7294 DOI:10.1038/ncomms8294.
Lange et al., "Classical Nuclear Localization Signals: Definition, Function, and Interaction with Importin", The Journal ol Biological Chemistry, 2007, 282:5101-5105.
Soderberg et al., "Direct observation of individual endogenous protein complexes in situ by proximity ligation", Nature Methods, 2006, 3(12):995-1000 DOI:10.1038/NMETH947.
Sternberg et al., "DNA interrogation by the CRISPR RNA-guided endonuclease Cas9", Nature, 2014, 507(7490):62-67, Figures 12 sheets.
Gomez et al., "Detection of histone modifications at specific gene loci in single cells in histological setions", Nature Methods, 10(2) 171-177 (2013).

(Continued)

*Primary Examiner* — Jennifer Dunston
(74) *Attorney, Agent, or Firm* — Sigma-Aldrich Co. LLC

(57) ABSTRACT

The present disclosure provides reagents and methods for molecular proximity detection of specific endogenous nucleic acids in situ using RNA-guided nucleic acid binding proteins.

3 Claims, 14 Drawing Sheets

Specification includes a Sequence Listing.

(56) References Cited

OTHER PUBLICATIONS

Wasserkort et al., "aberrant septin 9 DNA methylation in colorectal cancer is restricted to a single CpG island", BMC Cancer, 2013, 13:398.
Weibrecht et al., "In situ detection of individial mRNA molecules and protein complexes or post-translational modifications using padlock probes combines with the in situ proximity ligation assay", Nature Protocols 8.2 (2013):355-372.
Chen et al., "Dynamic Imaging of Genomic Loci in Living Human Cells by an Optimized CRISPR/Cas System", Cell 155, 1479-1491, Dec. 19, 2013.
International Search Report for PCT/US2015/67316 dated May 6, 2016 (5 pages).
International Search Report for PCT/US2016/53386 dated Feb. 3, 2017 (5 pages).

* cited by examiner

■ Duolink
■ DAPI
■ Actin

■ Duolink
■ DAPI

METHODS AND REAGENTS FOR MOLECULAR PROXIMITY DETECTION USING RNA-GUIDED NUCLEIC ACID BINDING PROTEINS

CROSS-REFERENCE TO RELATED APPLICATIONS

This application is a U.S. National Stage Application of PCT International Application No. PCT/US2016/053386, filed Sep. 23, 2016, which claims priority to U.S. Provisional Application Ser. No. 62/232,023, filed Sep. 24, 2015; the disclosure of each is hereby incorporated by reference in its entirety.

FIELD

The present disclosure generally relates to probes comprising RNA-guided nucleic acid binding proteins and use of complexes comprising said probes to detect endogenous nucleic acids in situ via molecular proximity.

BACKGROUND

Eukaryotic nuclear genomic DNA is packaged into chromatin and arranged in the nucleus as chromosomes. The spatial organization of chromatin and the relative positions of specific chromosomal regions are tightly associated with gene regulation during normal cell function and disease. Fluorescent in situ hybridization (FISH), a cytogenetic technique that uses fluorescent probes that bind to only those parts of the chromosome with a high degree of sequence complementarity, has been used to visualize specific chromatin domains, genes, or RNAs, including both messenger RNA (mRNA) and non-coding RNA (ncRNA). This technique, however, requires harsh treatment to denature the double-stranded genomic DNA for probe hybridization, and such treatment affects the integrity of chromatin structure and/or chromosomal organization and RNA secondary structure, stability and it's interactions with proteins and chromatin. Thus, there is a need for chromatin and RNA in situ imaging techniques that utilize milder reaction conditions and provide robust signal amplification.

SUMMARY

Among the various aspects of the present disclosure in the provision of a complex comprising at least one probe comprising (i) an engineered, non-naturally occurring Clustered Regularly Interspersed Short Palindromic Repeats (CRISPR)-associated (Cas) (CRISPR/Cas) system comprising a CRISPR/Cas protein and a guide RNA and (ii) an oligonucleotide that is linked directly or indirectly to the CRISPR/Cas system. In some embodiments, the CRISPR/Cas protein is a Cas9 protein. In some instances, the Cas9 protein comprises two functional nuclease domains, one functional nuclease domain, or no functional nuclease domain. In other embodiments, the Cas9 protein comprises at least one nuclear localization signal. In one embodiment, the Cas9 protein has no functional nuclease domain and is devoid of all nuclease activity. In another embodiment, the Cas9 protein is devoid of all nuclease activity and comprises at least one nuclear localization signal. In some embodiments, the complex comprises (a) a first probe comprising a CRISPR/Cas system and a first oligonucleotide that is linked to the CRISPR/Cas protein or the guide RNA of the CRISPR/Cas system by covalent or non-covalent bonds, and (b) a second probe comprising (i) a second CRISPR/Cas system and a second oligonucleotide that is linked to the CRISPR/Cas protein of the second CRISPR/Cas system by covalent or non-covalent bonds; (ii) a second CRISPR/Cas system and a second oligonucleotide that is linked to the guide RNA of the second CRISPR/Cas system by covalent or non-covalent bonds; or (iii) an antibody directed against a nucleic acid-associated protein or a nucleic acid modification and a second oligonucleotide that is linked to the antibody directed against the nucleic acid-associated protein or the nucleic acid modification. In further embodiments, the complex comprises (a) a first probe comprising a CRISPR/Cas system and a first oligonucleotide that is linked to a primary antibody directed against the CRISPR/Cas protein; and (b) a second probe comprising an antibody directed against a nucleic acid-associated protein or nucleic acid modification and a second oligonucleotide that is linked to the antibody directed against the nucleic acid-associated protein or the nucleic acid modification. In additional embodiments, the complex comprises a probe comprising a CRISPR/Cas system, first and second oligonucleotides that are linked to anti-species secondary antibodies, and primary antibodies directed against the CRISPR/Cas protein. In some iterations, the complex comprising the CRISPR/Cas containing probe comprising first and second linked to anti-species secondary antibodies further comprises at least one additional CRISPR/Cas system. In certain embodiments, the oligonucleotides of the complexes detailed above are single stranded and/or comprise stem, loop, and/or hairpin secondary structures. In other embodiments, the oligonucleotides of the complexes comprise deoxyribonucleotides, ribonucleotides, or combinations thereof, wherein the deoxyribonucleotides or ribonucleotides are standard nucleotides, nucleotide analogs, or 2'-O-methyl modified nucleotides.

A further aspect of the present disclosure encompasses kits comprising any one of the complexes detailed above.

Still another aspect of the present disclosure provides a method for detecting an endogenous nucleic acid in a cell. The method comprises contacting the cell with a proximity detection probe complex comprising at least one probe comprising an RNA-guided nucleic acid binding protein, wherein the RNA-guided nucleic acid binding protein is guided by RNA to the endogenous nucleic acid for binding, thereby forming a bound proximity detection probe complex, and visualizing the bound proximity detection probe complex via an in situ proximity-dependent amplification reaction to detect the endogenous nucleic acid. In some embodiments, the proximity detection probe complex comprises a first probe comprising a CRISPR/Cas system comprising a CRISPR/Cas protein and a guide RNA that is targeted to a first site in the endogenous nucleic acid, and a first proximity detection oligonucleotide that is linked to the CRISPR/Cas protein or the guide RNA of the CRISPR/Cas system by covalent or non-covalent bonds. In some embodiments, the CRISPR/Cas protein is a Cas9 protein. In some instances, the Cas9 protein comprises two functional nuclease domains, one functional nuclease domain, or no functional nuclease domain. In other embodiments, the Cas9 protein comprises at least one nuclear localization signal. In one embodiment, the Cas9 protein has no functional nuclease domain and is devoid of all nuclease activity. In another embodiment, the Cas9 protein is devoid of all nuclease activity and comprises at least one nuclear localization signal. In some embodiments, the proximity detection probe complex further comprises a second probe comprising (a) a second CRISPR/Cas system comprising a second guide RNA targeted to a second site in the endogenous nucleic acid and a second proximity detection oligonucleotide that is linked to the CRISPR/Cas protein of the second CRISPR/Cas system by covalent or non-covalent bonds; (b) a second CRISPR/Cas system comprising a second guide RNA targeted to a second site in the endogenous nucleic acid and a second proximity detection oligonucleotide that is linked to the second guide RNA of the second CRISPR/Cas system by covalent or non-covalent bonds; or (c) an antibody directed against a nucleic acid-associated protein or a nucleic acid modification and a second proximity detection oligonucleotide that is linked to the antibody directed against the nucleic acid-associated protein or the nucleic acid modification. In other embodiments, the proximity detection probe complex comprises a first probe comprising a CRISPR/Cas system comprising a CRISPR/Cas protein and a guide RNA that is targeted to a first site in the endogenous nucleic acid and a first proximity detection oligonucleotide that is a primary antibody directed against the CRISPR/Cas protein, and a second probe comprising an antibody directed against a nucleic acid-associated protein or a nucleic acid modification in the endogenous nucleic acid and a second proximity detection oligonucleotide that is linked to the antibody directed against the nucleic acid-associated protein or the nucleic acid modification. In additional embodiments, the proximity detection probe complex comprises a probe comprising a CRISPR/Cas system comprising a CRISPR/Cas protein and a guide RNA that is targeted to a first site in the endogenous nucleic acid, and first and second oligonucleotides that are linked to anti-species secondary antibodies, and the proximity detection probe complex further comprises primary antibodies directed against the CRISPR/Cas protein. In some iterations of this embodiment, the cell is contacted with a second or additional CRISPR/Cas system comprising a second or additional guide RNA directed to a second or additional site in the endogenous nucleic acid. In various embodiments, the endogenous nucleic acid is nuclear chromosomal DNA, messenger RNA, or non-coding RNA. In certain embodiments, the cell is a primary cell, a cell line cell, or within a tissue or fluid sample obtained from a subject. In other embodiments, the cell is live, fixed, or frozen. In additional embodiments, the in situ proximity-dependent amplification reaction comprises a proximity ligation assay (PLA) or a proximity-dependent initiation of hybridization chain reaction (proxHCR).

Other aspects and iterations of the disclosure are detailed below.

BRIEF DESCRIPTION OF THE FIGURES

FIG. 8A shows a cell contacted with minor satellite crRNA, and both anti-Cas9 and anti-CENP-A antibodies. FIG. 8B presents a cell contacted with negative control crRNA, and both anti-Cas9 and anti-CENP-A antibodies. FIG. 8C shows a cell contacted with minor satellite crRNA and anti-CENP-A antibodies. FIG. 8D presents a cell contacted with minor satellite crRNA and anti-Cas9 antibodies.

FIG. 10a shows a cell contacted with telomere crRNA, and both anti-Cas9 and anti-TRF2 antibodies. FIG. 10B presents a cell contacted with negative control crRNA and both anti-Cas9 and anti-TRF2 antibodies. FIG. 10C shows a cell contacted with telomere crRNA and anti-Cas9 antibodies. FIG. 10D presents a cell contacted with telomere crRNA and anti-TRF2 antibodies.

FIG. 11A shows a cell contacted with minor satellite crRNA, and both anti-Cas9 and anti-CENP-A antibodies. FIG. 11B presents a cell contacted with negative control crRNA, and both anti-Cas9 and anti-CENP-A antibodies. FIG. 11C shows a cell contacted with minor satellite crRNA and anti-Cas9 antibodies. FIG. 11D presents a cell contacted with minor satellite crRNA and anti-CENP-A antibodies.

DETAILED DESCRIPTION

Figure 1:
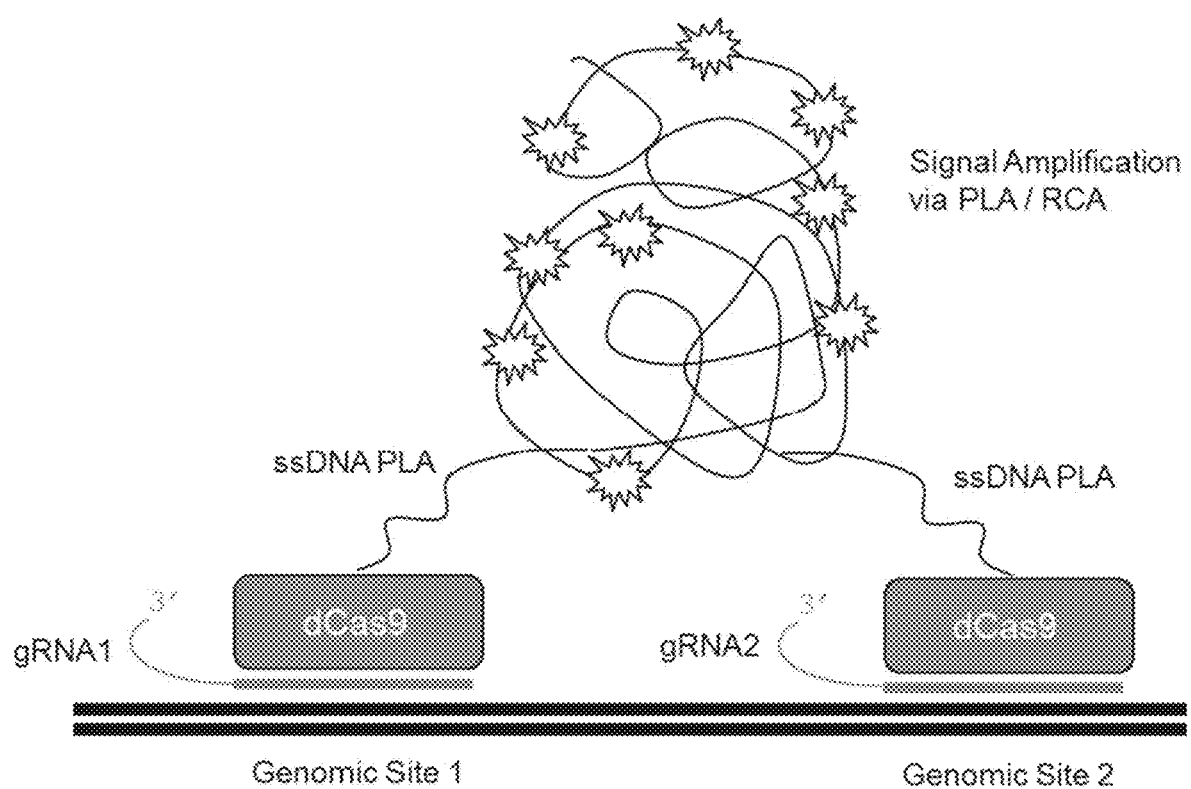
FIG. 1 diagrams detection of a genomic locus via proximal genomic binding of two dCas9-gRNA complexes and signal amplification via a proximity ligation assay (PLA). Signal amplification is initiated by single-stranded nucleic acid molecules bound covalently or non-covalently to the dCas9 proteins.

The present disclosure provides reagents and methods for molecular proximity detection of specific endogenous nucleic acids in situ using RNA-guided nucleic acid binding proteins. RNA-guided nucleic acid binding proteins such as those encoded by type II Clustered Regularly Interspersed Short Palindromic Repeats (CRISPR)-associated (Cas) (CRISPR/Cas) systems possess potent and flexible nucleic acid binding properties. The CRISPR/Cas system of *Streptococcus pyogenes* has been studied in great biochemical and structural detail with a focus on it enigmatic ability to unwind double-stranded DNA in the absence of any energy-dependent helicase activity (Sternberg et al., Nature, 2014, 506(7490):62-67). The CRISPR/Cas system has been used as a highly specific and efficient enzymatic probe for labeling repeated sequences of DNA in undisturbed nuclei of fixed cells and tissues (Deng et al., Proc Natl Acad Sci USA., 2015, 112(37):E5123-32). Herein, the detection capability of the CRISPR/Cas system is dramatically increased by proximity detection. Provided herein are proximity detection probe complexes comprising at least one CRISPR/Cas system, methods of using said proximity detection probe complexes to detect endogenous nucleic acids in situ, and kits comprising said proximity detection probe complexes.

I. Proximity Detection Probe Complexes

One aspect of the disclosure provides a proximity detection probe complex comprising an RNA-guided nucleic acid binding protein. The RNA-guided nucleic acid binding protein can be a CRISPR/Cas system comprising a CRISPR/Cas protein and a guide RNA (gRNA). The proximity detection probe complex disclosed herein comprises at least one probe comprising a CRISPR/Cas system, which directs binding of the probe to a target nucleic acid, and a proximity detection oligonucleotide, which facilitates detection of the bound probe via an amplifiable proximity detection assay. In general, the proximity detection oligonucleotide is linked directed or indirectly to the CRISPR/Cas system. In some embodiments, the proximity detection oligonucleotide can be linked directly to the CRISPR/Cas protein (see FIG. 1) or the guide RNA (see FIG. 4) of the probe. In other embodiments, the proximity detection oligonucleotide can be linked to an antibody directed against the CRISPR/Cas protein (see FIG. 3, probe at genomic site 1). In further embodiments, the proximity detection oligonucleotide(s) can be linked to anti-species secondary antibodies, and the proximity detection probe complex further comprises primary antibodies directed against the CRISPR/Cas protein (see FIGS. 5 and 6). The proximity detection probe complex can further comprise additional probes as detailed below.

(a) Probes Comprising CRISPR/Cas System

The proximity detection probe complex comprises at least one probe comprising a binding moiety comprising an RNA-guided nucleic acid binding protein and at least one proximity detection oligonucleotide. The RNA-guided nucleic acid binding protein can be a CRISPR/Cas system comprising a CRISPR/Cas protein and a guide RNA (i) CRISPR/Cas System The proximity detection probe complex disclosed herein comprises at least one probe comprising a CRISPR/Cas system. The CRISPR/Cas system can be a non-naturally occurring genetically engineered system CRISPR/Cas system. A CRISPR/Cas system comprises a CRISPR/Cas protein and a guide RNA.

CRISPR/Cas Proteins.

The CRISPR/Cas protein of the proximity detection probe complex can be derived from a type I (i.e., IA, IB, IC, ID, IE, or IF), type II (i.e., IIA, IIB, or IIC), type III (i.e., IIIA or IIIB), or type V CRISPR system, which are present in various bacteria and archaea. The CRISPR/Cas system can be from *Streptococcus* sp. (e.g., *Streptococcus pyogenes*), *Campylobacter* sp. (e.g., *Campylobacter jejuni*), *Francisella* sp. (e.g., *Francisella novicida*), *Acaryochloris* sp., *Acetohalobium* sp., *Acidaminococcus* sp., *Acidithiobacillus* sp., *Alicyclobacillus* sp., *Allochromatium* sp., *Ammonifex* sp., *Anabaena* sp., *Arthrospira* sp., *Bacillus* sp., *Burkholderiales* sp., *Caldicelulosiruptor* sp., *Candidatus* sp., *Clostridium* sp., *Crocosphaera* sp., *Cyanothece* sp., *Exiguobacterium* sp., *Finegoldia* sp., *Ktedonobacter* sp., *Lactobacillus* sp., *Lyngbya* sp., *Marinobacter* sp., *Methanohalobium* sp., *Microscilla* sp., *Microcoleus* sp., *Microcystis* sp., *Natranaerobius* sp., *Neisseria* sp., *Nitrosococcus* sp., *Nocardiopsis* sp., *Nodularia* sp., *Nostoc* sp., *Oscillatoria* sp., *Polaromonas* sp., *Pelotomaculum* sp., *Pseudoalteromonas* sp., *Petrotoga* sp., *Prevotella* sp., *Staphylococcus* sp., *Streptomyces* sp., *Streptosporangium* sp., *Synechococcus* sp., or *Thermosipho* sp.

Non-limiting examples of suitable CRISPR/Cas proteins include Cas proteins, Cpf proteins, Cmr proteins, Csa proteins, Csb proteins, Csc proteins, Cse proteins, Csf proteins, Csm proteins, Csn proteins, Csx proteins, Csy proteins, Csz proteins, and derivatives or variants thereof. In specific embodiments, the CRISPR/Cas protein can be a type II Cas9 protein, a type V Cpf1 protein, or a derivative thereof. In some embodiments, the CRISPR/Cas protein can be *Streptococcus pyogenes* Cas9 (SpCas9) or *Streptococcus thermophilus* Cas9 (StCas9). In other embodiments, the CRISPR/Cas protein can be *Campylobacter jejuni* Cas9 (CjCas9). In alternate embodiments, the CRISPR/Cas protein can be *Francisella novicida* Cas9 (FnCas9). In yet other embodiments, the CRISPR/Cas protein can be *Francisella novicida* Cpf1 (FnCpf1).

The CRISPR/Cas protein can comprise at least one RNA recognition domain and/or RNA binding domain, which interact with the guide RNA. The CRISPR/Cas protein can also comprise nuclease domains (i.e., DNase or RNase domains), DNA binding domains, helicase domains, RNAse domains, protein-protein interaction domains, dimerization domains, as well as other domains.

In some embodiments, the CRISPR/Cas protein can be derived from a wild type Cas9 protein or fragment thereof. In general, Cas9 proteins comprise at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek et al., Science, 2013, 337:816-821). In other embodiments, the CRISPR/Cas protein can be derived from modified Cas9 protein. For example, a Cas9 protein or derivative thereof can be modified to contain only one functional nuclease domain (either a RuvC-like or a HNH-like nuclease domain). In particular, the Cas9-derived protein or derivative thereof can be modified such that one of the nuclease domains is deleted or mutated such that the nuclease domain is no longer functional (i.e., the nuclease activity is absent). In embodiments in which one of the nuclease domains is inactive, the Cas9 protein is able to cleave one strand of double-stranded DNA (i.e., such protein is termed a "nickase"). A nickase is not able to create a double-stranded break in DNA. For example, an aspartate to alanine (D10A) conversion in a RuvC-like domain converts the Cas9 protein or derivative thereof into a nickase. Likewise, a histidine to alanine (H840A or H839A) conversion in a HNH domain converts the Cas9 protein or derivative thereof into a nickase. In further embodiments, both the RuvC-like nuclease domain and the HNH-like nuclease domain can be modified or eliminated such that the Cas9 protein or derivative thereof is unable to nick or cleave double stranded nucleic acid (such protein is termed dead Cas9 or dCas9). For example, the Cas9 protein can comprise D10A and H840A (or D10A and H839A) mutations. In some embodiments, all nuclease domains of a Cas9 protein or derivative thereof can be modified or eliminated such that the derived protein lacks all nuclease activity.

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In some embodiments, the CRISPR/Cas protein can further comprise at least one nuclear localization signal. In general, an NLS comprises a stretch of basic amino acids. Nuclear localization signals are known in the art (see, e.g., Lange et al., J. Biol. Chem., 2007, 282:5101-5105). For example, in one embodiment, the NLS can be a monopartite sequence, such as PKKKRKV (SEQ ID NO:1) or PKKKRRV (SEQ ID NO:2). In another embodiment, the NLS can be a bipartite sequence, such as KRPAATKK-AGQAKKKK (SEQ ID NO:3). The NLS can be located at the N-terminus, the C-terminal, or in an internal location of the CRISPR/Cas protein.

In still other embodiments, the CRISPR/Cas protein can further comprise at least one cell-penetrating domain. In one embodiment, the cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO:4). In another embodiment, the cell-penetrating domain can be TLM (PLSSIFSRIGDPPKKKRKV; SEQ ID NO:5), a cell-penetrating peptide sequence derived from the human hepatitis B virus. In still another embodiment, the cell-penetrating domain can be MPG (GALFLGWLGAAGSTMGAPKKKRKV; SEQ ID NO:6 or GALFLGFLGAAGSTMGAWSQPKKKRKV; SEQ ID NO:7). In an additional embodiment, the cell-penetrating domain can be Pep-1 (KETWWETWWTEWS-QPKKKRKV; SEQ ID NO:8), VP22, a cell penetrating peptide from Herpes simplex virus, or a polyarginine peptide sequence. The cell-penetrating domain can be located at the N-terminus, the C-terminus, or in an internal location of the CRISPR/Cas protein.

In still other embodiments, the CRISPR/Cas protein can also comprise at least one marker domain. Non-limiting examples of marker domains include fluorescent proteins, purification tags, and epitope tags. In some embodiments, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato) or any other suitable fluorescent protein. In other embodiments, the marker domain can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin. The marker domain can be located at the N-terminus or the C-terminus of the CRISPR/Cas protein.

The CRISPR/Cas protein can be obtained from commercial sources. Alternatively, DNA encoding the CRISPR/Cas protein can be cloned into an expression vector and the CRISPR/Cas protein can be expressed and purified from bacterial or eukaryotic cells using standard procedures. In still other embodiments, the CRISPR/Cas protein can be provided as an encoding nucleic acid. For example, the encoding nucleic acid can be messenger RNA. Alternatively, the encoding nucleic acid can be DNA (e.g., can be part of a vector), wherein the coding DNA can be operably linked to a suitable promoter control sequence (e.g., eukaryotic/mammalian promoters such as CMV, SV40, RSV, MMTV). The encoding nucleic acid can be codon optimized for expression in the cell of interest.

Guide RNA.

The CRISPR/Cas system also comprises a guide RNA. The guide RNA interacts with the CRISPR/Cas protein to direct the CRISPR/Cas protein to a specific target site in a chromosomal sequence or endogenous nucleic acid, wherein the 5' end of the guide RNA base pairs with a specific protospacer sequence in the target sequence.

The target site has no sequence limitation except that the sequence is immediately followed (downstream) by a consensus sequence. This consensus sequence is also known as a protospacer adjacent motif (PAM). For example, PAM sequences for Cas9 include 3'-NGG, 3'-NGGNG, 3'-NNA-GAAW, and 3'-ACAY and PAM sequences for Cpf1 include 5'-TTN (wherein N is defined as any nucleotide, W is defined as either A or T, and Y is defined an either C or T). In some embodiments, the target site can be in the coding region of a gene, in an intron of a gene, in a control region of a gene, in a spacer region between genes, in a non-coding region, etc. The gene can be a protein coding gene or an RNA coding gene. In other embodiments, the target site can be in an RNA molecule.

Each guide RNA comprises three regions: a first region at the 5' end that is complementary to the target site in the nucleic acid sequence, a second internal region that forms a stem loop structure, and a third 3' region that remains essentially single-stranded. The first region (at the 5' end) of each guide RNA is different such that each guide RNA guides the CRISPR/Cas protein to a specific target site. The second and third regions of each guide RNA can be the same in all guide RNAs.

The first region of the guide RNA is complementary to the target site in the nucleic acid sequence such that the first region of the guide RNA is able to base pair with the target site. The first region of each guide RNA (also called crRNA) comprises a sequence that is complementary to the target sequence. In various embodiments, the first region of the guide RNA can comprise from about 10 nucleotides to more than about 25 nucleotides. For example, the region of base pairing between the first region of the guide RNA and the target site in the nucleic acid sequence can be about 10, 11, 12, 13, 14, 15, 16, 17, 18, 19, 20, 22, 23, 24, 25, or more than 25 nucleotides in length. In specific embodiments, the first region of the guide RNA is about 20 nucleotides in length. As an example, a Cas9 gRNA can comprise $GN_{17-20}GG$.

In one embodiment, multiple non-overlapping unique crRNAs can be designed to tile the targeted endogenous nucleic acid. For example, multiple crRNAs can be used to tile both strands of a 2 kb genomic target region. Ensuing recruitment of multiple CRISPR/Cas systems to the targeted genomic locus would provide greater topological chromatin landscape in three dimensions and facilitate proximity detection of the genomic locus of interest.

The guide RNA also comprises a second region that forms a secondary structure. In some embodiments, the secondary structure comprises a stem (or hairpin) and a loop. The length of the loop and the stem can vary. For example, the loop can range from about 3 to about 10 nucleotides in length, and the stem can range from about 6 to about 20 base pairs in length. The stem can comprise one or more bulges of 1 to about 10 nucleotides. Thus, the overall length of the second region can range from about 16 to about 60 nucleotides in length. In specific embodiments, the loop is about 4 nucleotides in length and the stem comprises about 12 base pairs.

The tracrRNA can be tagged at the 5' end with the digoxigenin (DIG) epitope to provide another antibody (anti-DIG) to detect the CRISPR/Cas system as the tracrRNA is universal to each CRISPR/Cas system.

The guide RNA also comprises a third region at the 3' end that remains essentially single-stranded. Thus, the third region has no complementarity to any nucleic acid sequence in the cell of interest and has no complementarity to the rest of the guide RNA. The length of the third region can vary. In general, the third region is more than about 4 nucleotides in length. For example, the length of the third region can range from about 5 to about 30 nucleotides in length.

In some embodiments, the guide RNA comprises a single molecule. In other embodiments, the guide RNA can comprise two separate molecules. The first RNA molecule (also called crRNA) can comprise the first region of the guide RNA and one half of the "stem" of the second region of the guide RNA. The second RNA molecule (also called tracrRNA) can comprise the other half of the "stem" of the second region of the guide RNA and the third region of the guide RNA. Thus, in this embodiment, the first and second RNA molecules each contain a sequence of nucleotides that are complementary to one another. For example, in one embodiment, the first and second RNA molecules each comprise a sequence (of about 6 to about 20 nucleotides) that base pairs to the other sequence.

The guide RNA can comprise standard ribonucleotides or ribonucleotide analogs. A nucleotide analog refers to known analogs of natural nucleotides, as well as nucleotides that are modified in the base, sugar, and/or phosphate moieties. In some embodiments, the guide RNA can comprise 2'-O-methyl nucleotides.

Guide RNAs can be synthesized chemically using standard oligonucleotide synthesis procedures. For example, crRNAs can be synthesized chemically. Alternatively, guide RNAs can be synthesized via in vitro transcription. For this, DNA encoding the guide RNA can be operably linked to a promoter sequence (e.g., T7, T3, or SP6 promoter) and the guide RNA can be produced in vitro by a polymerase (e.g., T7, T3, or SP6 RNA polymerase). In some embodiments, crRNAs can be chemically synthesized and tracrRNAs can be transcribed in vitro. Alternatively, guide RNAs can be provided as encoding DNA molecules for expression in the eukaryotic cell of interest. For example, DNA encoding the guide RNA can be operably linked to a promoter sequence that is recognized by RNA polymerase III (Pol III). Examples of suitable Pol III promoters include, but are not limited to, mammalian U6, U3, H1, and 7SL RNA promoters.

(ii) Proximity Detection Oligonucleotides

The CRISPR/Cas-containing probe of the proximity detection probe complex also comprises a proximity detection oligonucleotide. The proximity detection oligonucleotide can be linked directly or indirectly to the CRISPR/Cas system of the probe.

In some embodiments, the proximity detection oligonucleotide can be a single-stranded nucleic acid. In other embodiments, the proximity detection oligonucleotide can comprise single-stranded and double-stranded regions. That is, the proximity detection oligonucleotide can comprise stems, loops, and/or hairpin regions.

The proximity detection oligonucleotide can comprise deoxyribonucleotides, ribonucleotides, or combinations thereof. The deoxyribonucleotides/ribonucleotides can be standard nucleotides or nucleotide analogs. A nucleotide analog refers to known analogs of natural nucleotides (e.g., inosine), as well as nucleotides that are modified in the base, sugar, and/or phosphate moieties (e.g., phosphorothioate). In some embodiments, the 3' end of the proximity detection oligonucleotide can comprise one or more blocking nucleotides. Non-limiting examples of suitable blocking nucleotides include 2'-O-methyl nucleotides, 2'-fluoro nucleotides, 3'-$ONH_2$ nucleotides, dideoxy nucleotides, and propyne nucleotides. In specific embodiments, the 3' terminal end of the proximity detection oligonucleotide can comprise three 2'-O-methyl ribonucleotides.

The length of the proximity detection oligonucleotide can and will vary. In general, the proximity detection oligonucleotide can range from about 15 nucleotides to about 200 nucleotides in length. In some embodiments, the proximity detection oligonucleotide can range from about 20 nucleotides to about 100 nucleotides in length. In other embodiments, proximity detection oligonucleotide can range from about 30 nucleotides to about 60 nucleotides in length.

The proximity detection oligonucleotide can be obtained commercially. Alternatively, the proximity detection oligonucleotide can be synthesized using standard oligonucleotide synthesis procedures.

In some embodiments, the proximity detection oligonucleotide can be linked directly to the CRISPR/Cas protein of the CRISPR/Cas system of the probe (see FIG. 1). The linking can be via covalent or non-covalent bonds. For example, the proximity detection oligonucleotide can be linked to the CRISPR-Cas protein by a covalent bond. The bonding can be direct or via a linker or an adapter molecule. Techniques for covalently linking an oligonucleotide to a protein are well known in the art. Alternatively, the proximity detection oligonucleotide can be linked to the CRISPR-Cas protein by a non-covalent bond. For example, the proximity detection oligonucleotide could be bound to the CRISPR/Cas protein via hydrogen or ionic bonds.

Figure 4:
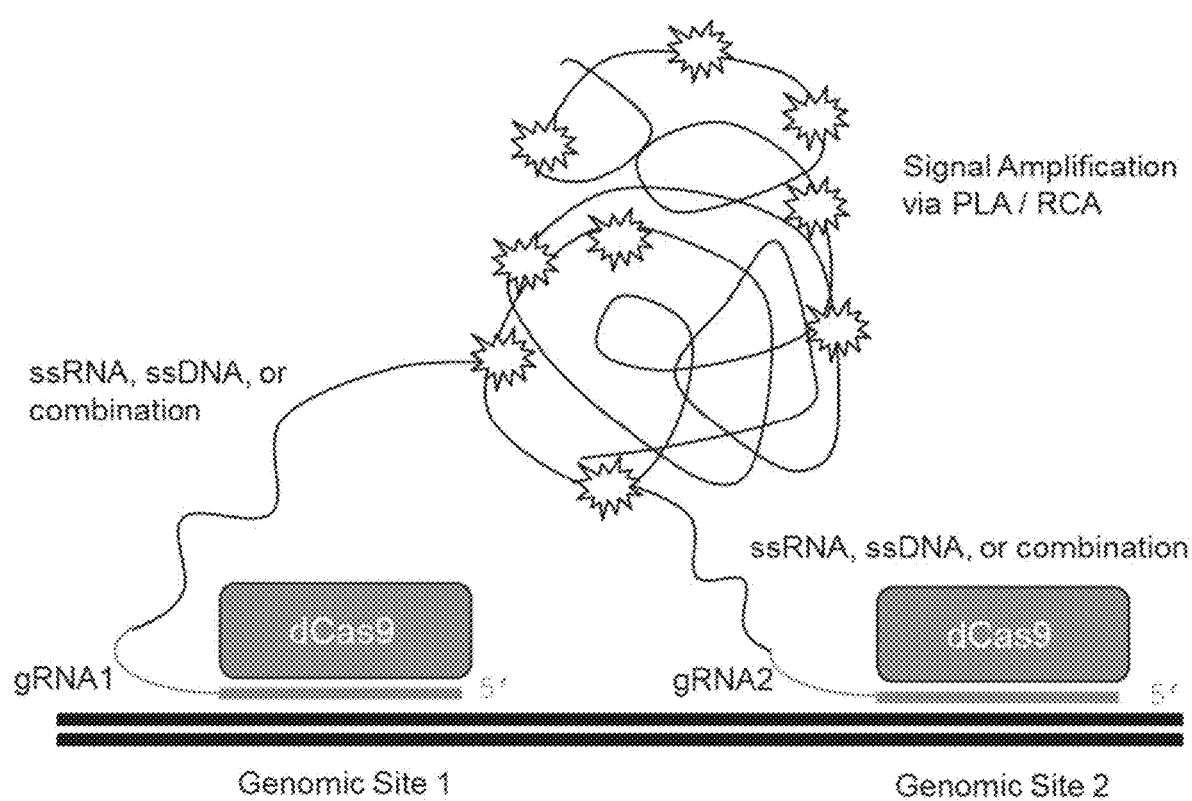
FIG. 4 illustrates detection of a genomic locus via proximal genomic binding of two PLA-compatible Cas9-gRNA complexes in which the PLA signal is initiated by single-stranded nucleic acid molecules covalently or non-covalently bound to the gRNA molecules.

In other embodiments, the proximity detection oligonucleotide can be linked directly to the guide RNA of the CRISPR/Cas system of the probe (see FIG. 4). The linking can be via covalent or non-covalent bonds. For example, the proximity detection oligonucleotide can be linked to the 3' end, 5' end, or an internal nucleotide of the guide RNA by a covalent bond. Alternatively, the proximity detection oligonucleotide can be linked to the guide RNA by a non-covalent bond. For example, the proximity detection oligonucleotide could base pair with a region at the 3' end of the guide RNA.

In additional embodiments, the proximity detection oligonucleotide can be linked indirectly to the CRISPR/Cas system of the probe. For example, the proximity detection oligonucleotide can be linked to a primary antibody directed against the CRISPR/Cas protein (see FIG. 3, probe at genomic site 1). The anti-CRISPR/Cas protein antibody can be a polyclonal antibody or a monoclonal antibody. The linkage between the proximity detection oligonucleotide and the antibody can be via covalent or non-covalent bonds. In some embodiments, the proximity detection oligonucleotide can be linked to the antibody via a covalent bond. The linkage can be direct or via a linker or an adapter molecule. Techniques for linking or conjugating oligonucleotides to proteins or antibodies are well known in the art. In other embodiments, the proximity detection oligonucleotide can be linked to the anti-CRISPR/Cas antibody by a non-covalent bond. For example, the proximity detection oligonucleotide could be bound to the antibody via hydrogen or ionic bonds In still other embodiments in which the proximity detection oligonucleotide is linked indirectly to the CRISPR/Cas system, the first (and second) proximity detection oligonucleotides can be linked to anti-species secondary antibodies (and the proximity detection probe complex further comprises a primary antibody directed against the CRISPR/Cas protein) (see FIGS. 5 and 6). The linkage between the proximity detection oligonucleotide and the antibody can be via covalent or non-covalent bonds (as detailed above). The anti-species secondary antibodies are directed against the species (e.g., rabbit, mouse, etc.) in which the anti-CRISPR/Cas protein antibodies are generated. In instances in which the complex comprises more than one proximity detection oligonucleotide linked to anti-species secondary antibodies, the sequences and/or structures of the more than one proximity detection oligonucleotides differ. In specific embodiments, the complex comprises first and second proximity detection oligonucleotides linked to anti-species secondary antibodies, wherein the sequence and/or structure of the first proximity detection oligonucleotide differs from that of the second proximity detection oligonucleotide.

(iii) Specific First Probes Comprising the CRISPR/Cas-Like Protein

In some embodiments, the first probe of the proximity detection probe complex comprises the CRISPR/Cas system, and a first oligonucleotide that is linked to the CRISPR/Cas protein or the guide RNA of the CRISPR/Cas system by covalent or non-covalent bonds. In alternate embodiments, the first probe of the proximity detection probe complex comprises the CRISPR/Cas system, and a first oligonucleotide that is linked to an antibody directed against the CRISPR/Cas protein. In still other embodiments, the first probe of the proximity detection probe complex comprises the CRISPR/Cas system, and at least one oligonucleotide that is linked to anti-species secondary antibodies, and the complex further comprises primary antibodies directed against the CRISPR/Cas protein. In some embodiments, the CRISPR/Cas protein of the CRISPR/Cas system is a Cas9 protein. In various embodiments, the Cas9 protein has nuclease activity, has nickase activity, or is modified to lack all nuclease activity. In some embodiments, the Cas9 protein is modified to lack all nuclease activity. In other embodiments, the Cas9 protein comprises at least one nuclear localization signal.

(b) Additional Probes

The proximity detection probe complex generally further comprises one or more additional probes. The second (or additional) probe comprises a binding moiety, which can be a CRISPR/Cas system comprising a different guide RNA, and a second (or additional) additional proximity detection oligonucleotide whose sequence and/or structure differs from that of the first proximity detection oligonucleotide. For example, the first or second proximity detection probe oligonucleotide can comprise one or more blocking nucleotides at the 3' terminal end of the oligonucleotide. Alternatively, the first or second proximity detection probe oligonucleotides can comprise different sequences and/or different hairpin structures. In some instances, the first and second proximity detection oligonucleotides can be called (+) and (−) oligonucleotides.

In embodiments in which the first proximity detection oligonucleotide of the first probe is linked directly to the CRISPR/Cas system (i.e., via the CRISPR/Cas protein or the guide RNA), the proximity detection probe complex can further comprise a second probe. The second probe comprises a binding moiety and a second proximal detection oligonucleotide, wherein the second proximal detection oligonucleotide has a different sequence and/or structure from that of the first proximal detection oligonucleotide of the first probe. In some embodiments, the binding moiety of the second probe can be another CRISPR/Cas system, and the second proximity detection oligonucleotide can be linked to the CRISPR/Cas protein or the guide RNA of the second CRISPR/Cas system of the second probe by covalent or non-covalent bonds (see FIG. 1 and FIG. 4) In other embodiments, the binding moiety of the second probe can be an antibody directed against a nucleic acid-associated protein or a nucleic acid modification, and the second proximity detection oligonucleotide can be linked to the antibody directed against the nucleic acid-associated protein or the nucleic acid modification (see FIG. 2). The nucleic acid-associated protein can be a general transcription factor, a specific transcription factor, a transcription regulatory protein, a chromatin binding protein, a chromatin remodeling protein or enzyme, a chromatin modification enzyme (e.g., methyltransferase, acetyltransferase, etc.), a DNA-binding protein, a histone protein, a modified histone protein, a splicing protein/factor, a RNA modification protein, a RNA processing protein, a RISC protein, a RNA-binding protein, a non-coding RNA processing factor, and the like. The nucleic acid modification can be a deoxyribonucleotide or ribonucleotide modified by methylation, hydroxylation, acetylation, formylation, acylation, carboxylation, thiolation, alkylation, amination, esterification, phosphorylation, or combinations thereof.

In embodiments in which the first proximity detection oligonucleotide is linked indirectly to the CRISPR/Cas system via an anti-CRISPR/Cas antibody, the proximity detection probe complex can further comprise a second probe. The second probe comprises a binding moiety and a second proximal detection oligonucleotide, wherein the sequence and/or structure of the second proximal detection oligonucleotide differ from that of the first proximal detection oligonucleotide of the first probe. In some embodiments, the binding moiety of the second probe can be an antibody directed against a nucleic acid-associated protein or a nucleic acid modification (as detailed above), and the second proximity detection oligonucleotide can be linked to an antibody directed against the nucleic acid-associated protein or the nucleic acid modification (see FIG. 3, genomic site 2).

In other embodiments in which the first proximity detection oligonucleotide is linked indirectly to the CRISPR/Cas system via anti-species secondary antibodies, the proximity detection probe complex can further comprise a second proximity oligonucleotide linked to the anti-species antibodies (see FIG. 5), wherein the sequences and/or structures of the first and second proximity detection oligonucleotides differ. In additional embodiments in which the proximity detection probes are linked to anti-species antibodies, the complex can further comprise one or more CRISPR/Cas systems, which can be indirectly linked to proximity detection oligonucleotides via the anti-species antibodies (see FIG. 6). Each CRISPR/Cas system comprises a different guide RNA.

Table A list various combinations of first and second probes.

TABLE A

| Example Complexes | First probe | Second probe |
|---|---|---|
| 1 | Cas system w/1$^{st}$ oligo linked to Cas protein | Cas system w/2$^{nd}$ oligo linked to Cas protein |
| 2 | Cas system w/1$^{st}$ oligo linked to Cas protein | Cas system w/2$^{nd}$ oligo linked to gRNA |
| 3 | Cas system w/1$^{st}$ oligo linked to Cas protein | Anti-chromosomal Ab w/2$^{nd}$ oligo linked to anti-chromosomal Ab |
| 4 | Cas system w/1$^{st}$ oligo linked to gRNA | Cas system w/2$^{nd}$ oligo linked to Cas protein |
| 5 | Cas system w/1$^{st}$ oligo linked to gRNA | Cas system w/2$^{nd}$ oligo linked to gRNA |
| 6 | Cas system w/1$^{st}$ oligo linked to gRNA | Anti-chromosomal Ab w/2$^{nd}$ oligo linked to anti-chromosomal Ab |
| 7 | Cas system w/1$^{st}$ oligo linked to anti-Cas Ab | Anti-chromosomal Ab w/2$^{nd}$ oligo linked to anti-chromosomal Ab |
| 8 | Cas system w/1$^{st}$ oligo linked to anti-species Ab (complex comprises anti-Cas Ab) | 2$^{nd}$ oligo linked to anti-species Ab |
| 9 | Cas system w/1$^{st}$ and 2$^{nd}$ oligos linked to anti-species Ab (complex comprises anti-Cas Ab) | Additional Cas systems |

II. Methods for Detecting Endogenous Nucleic Acids

Another aspect of the present disclosure encompasses a method for detecting and visualizing an endogenous nucleic acid in situ in a cell. The method comprises contacting the cell with a proximity detection probe complex comprising at least one probe comprising an RNA-guided nucleic acid binding protein, wherein the RNA-guided nucleic acid binding protein is guided by RNA to the endogenous nucleic acid for binding, thereby forming a bound proximity detection probe complex, and visualizing the bound proximity detection probe complex via an in situ proximity-dependent amplification reaction to detect the endogenous nucleic acid.

In general, the proximity detection probe complex comprises a first probe comprising a CRISPR/Cas system directed to a first site in the endogenous nucleic acid and a first proximity detection oligonucleotide that is linked directly or indirectly to the CRISPR/Cas system. In some embodiments, the CRISPR/Cas protein of the CRISPR/Cas system is a Cas9 protein. In various embodiments, the Cas9 protein has nuclease activity, has nickase activity, or is modified to lack all nuclease activity. In some embodiments, the Cas9 protein is modified to lack all nuclease activity. In other embodiments, the Cas9 protein comprises at least one nuclear localization signal. Generally, the complex further comprises a second probe comprising a binding moiety (which can be another CRISPR/Cas system directed to a proximal second site in the endogenous nucleic acid or an antibody directed to a proximally located protein or a nucleic acid modification) and a second proximity detection oligonucleotide that differs from the first proximity detection oligonucleotide and is linked directly or indirectly to the binding moiety. Upon binding, the first and second probes of the proximity detection probe complex are proximally located and can be detected and visualized via an in situ proximity-dependent amplification reaction. The in situ proximity-dependent amplification reaction can be a proximity ligation assay (PLA, see Söderberg, et al., Nature Methods, 2006, 2(12):995-1000) or a proximity-dependent initiation of hybridization chain reaction (proxHCR, see Koos et al., Nature Communications, 2015, 6:7294|DOI: 10.1038/ncomms8294).

(a) Contacting the Cell with a Proximity Detection Probe Complex

The method comprises contacting the cell with a proximity detection probe complex comprising at least one probe comprising a CRISPR/Cas system. Proximity detection probe complexes are described above in section (I).

In some embodiments, the cell can be contacted with a proximity detection probe complex comprising (a) a first probe comprising a first CRISPR/Cas system targeted to a first site in the endogenous nucleic acid and a first proximity detection oligonucleotide that is linked directly to the CRISPR/Cas protein or the guide RNA of the first CRISPR/Cas system and (b) a second probe comprising a second CRISPR/Cas system targeted to a second site in the endogenous nucleic acid and a second proximity detection oligonucleotide that is directly linked to the CRISPR/Cas protein or the guide RNA of the second CRISPR/Cas system (see complexes 1, 2, 4, and 5 in Table A and FIGS. 1 and 4).

Figure 2:
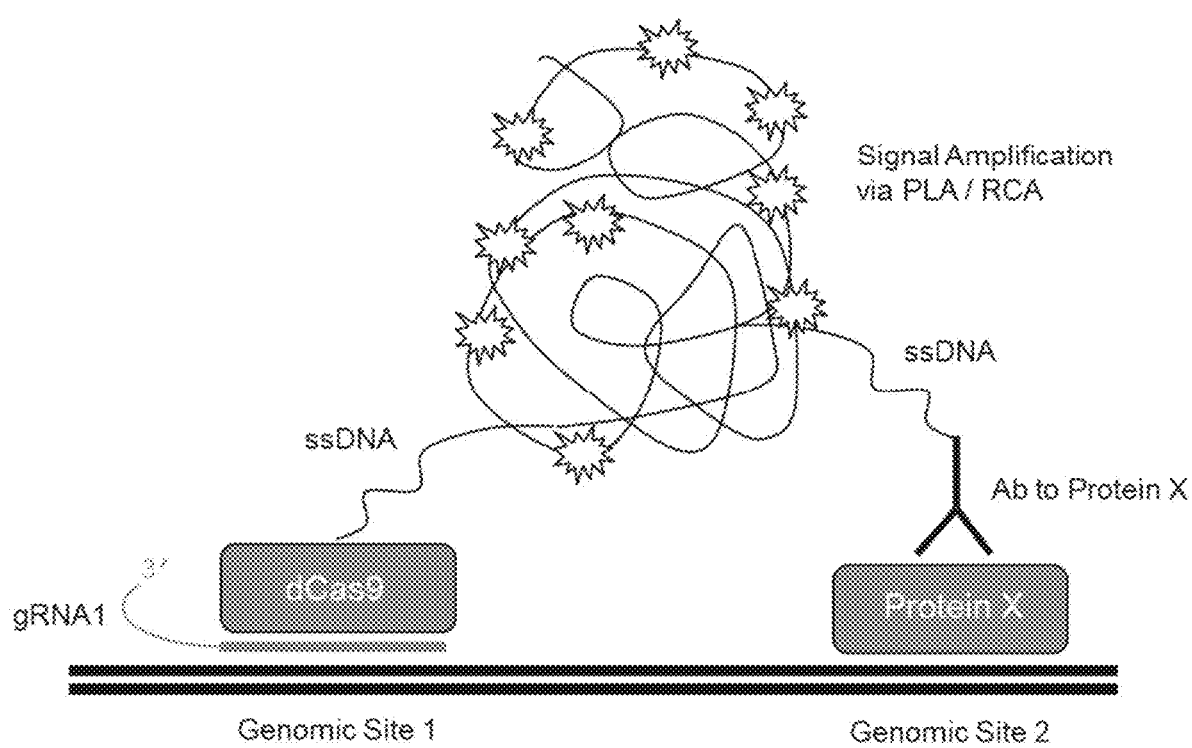
FIG. 2 illustrates detection of a genomic locus and proximal protein X via proximal genomic binding a PLA-compatible dCas9-gRNA complex and a PLA-compatible antibody to proximal protein X, and PLA-based signal amplification.

In other embodiments, the cell can be contacted with a proximity detection probe complex comprising (a) a first probe comprising a CRISPR/Cas system targeted to a first site in the endogenous nucleic acid and a first proximity detection oligonucleotide that is linked directly to the CRISPR/Cas protein or the guide RNA of the first CRISPR/Cas system and (b) a second probe comprising an antibody directed against a proximally-located protein associated with the endogenous nucleic acid or an antibody directed against a nucleic acid modification in the endogenous nucleic acid and a second proximity detection oligonucleotide that is linked to the antibody directed against the nucleic acid-associated protein or the antibody directed against the nucleic acid modification (see complexes 3 and 6 in Table A and FIG. 2).

Figure 3:
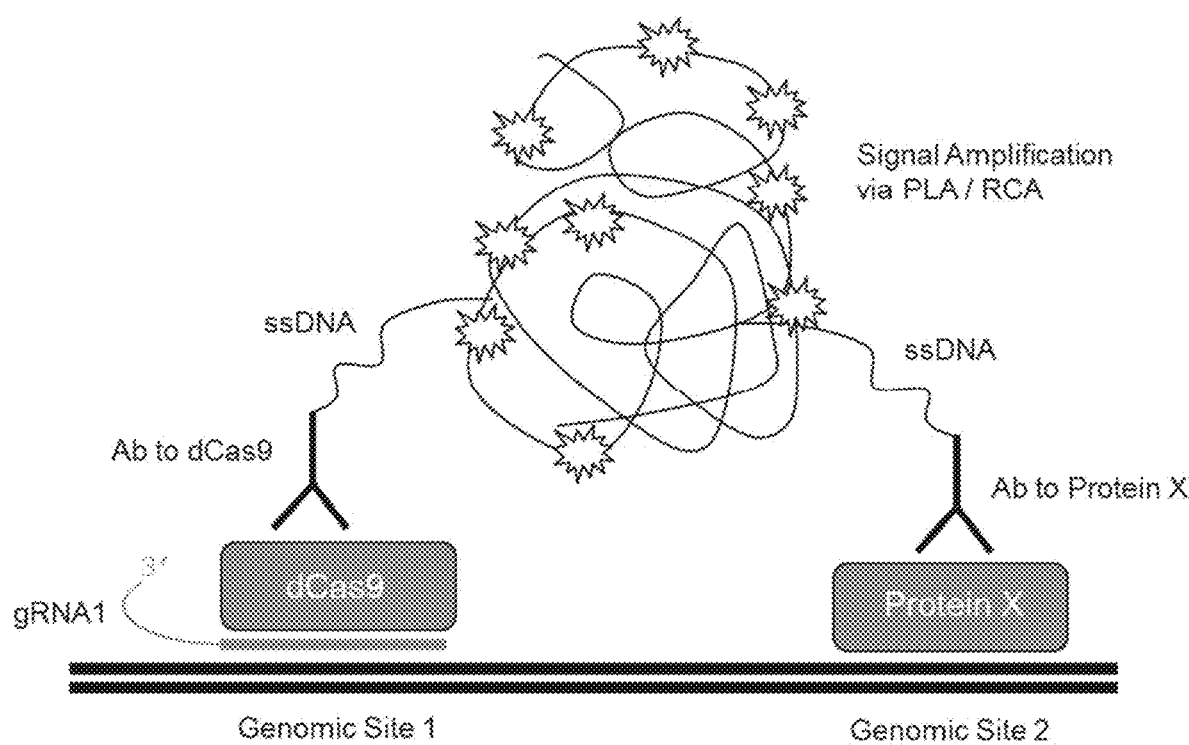
FIG. 3 diagrams detection of a genomic locus and proximal protein X via proximal genomic binding a dCas9-gRNA complex and a PLA-compatible antibody to proximal protein X. PLA-based amplification utilizes a PLA-compatible anti-Cas9 antibody.

In other embodiments, the cell can be contacted with a proximity detection probe complex comprising (a) a first probe comprising a CRISPR/Cas system targeted to a first site in the endogenous nucleic acid and a first proximity detection oligonucleotide that is linked to a primary antibody directed against the CRISPR/Cas protein and (b) a second probe comprising an antibody directed against a proximally-located protein associated with the endogenous nucleic acid or an antibody directed against a nucleic acid modification in the endogenous nucleic acid and a second proximity detection oligonucleotide that is linked to the antibody directed against the nucleic acid-associated protein or the antibody directed against the nucleic acid modification (see complex 7 in Table A and FIG. 3).

Figure 5:
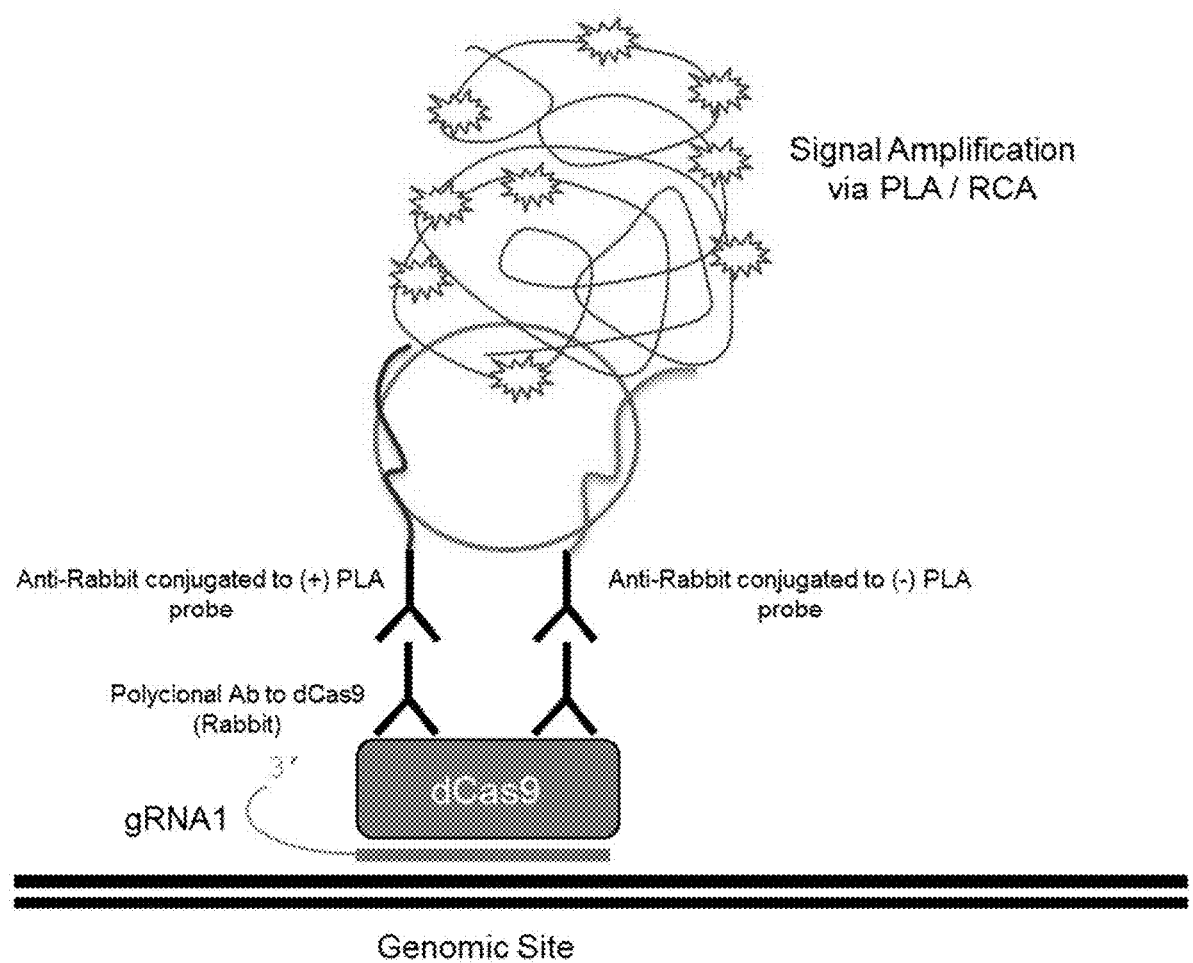
FIG. 5 diagrams detection of a genomic locus using a dCas9-gRNA complex and initiation of signal amplification via PLA using polyclonal (rabbit) anti-Cas9 antibodies and anti-rabbit PLA (+) and (−) probes.
Figure 6:
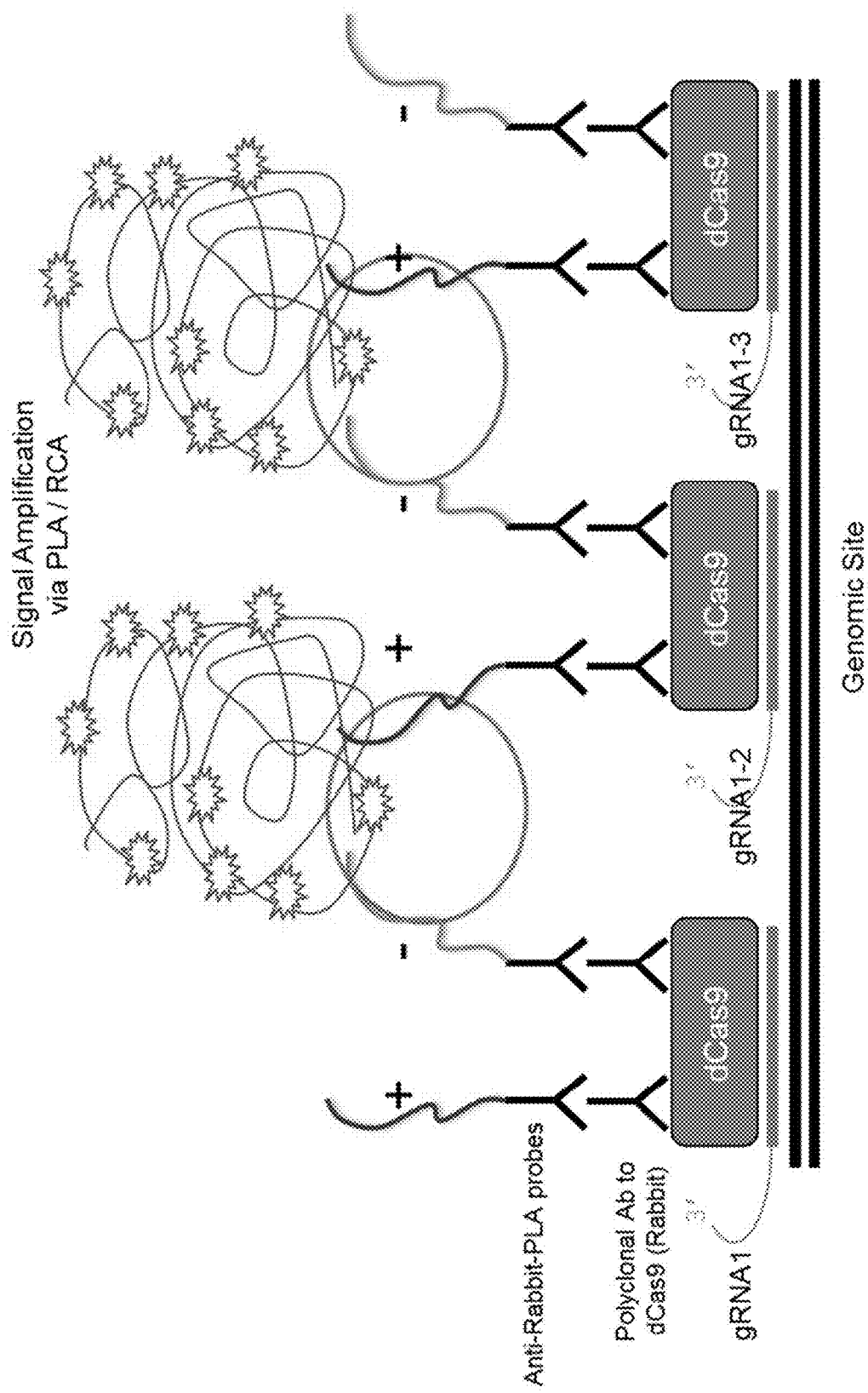
FIG. 6 illustrates detection of a genomic locus using dCas9-gRNA complexes (assembled with gRNAs that tile the genomic locus) and initiation of signal amplification via PLA using polyclonal (rabbit) anti-Cas9 antibodies and anti-rabbit PLA (+) and (−) probes.

In further embodiments, the cell can be contacted with a proximity detection probe complex comprising a probe comprising a CRISPR/Cas system targeted to a first site in the endogenous nucleic acid, and first and second proximity detection oligonucleotides linked to anti-species secondary antibodies, wherein the proximity detection probe complex further comprises primary antibodies directed against the CRISPR/Cas protein (see complex 8 in Table A and FIG. 5). In some iterations of this embodiment, the cell can be contacted with a second or additional CRISPR/Cas system(s) directed to a second or additional site(s) in the endogenous nucleic acid, wherein the CRISPR/Cas system(s) can be indirectly linked to the first and second proximity detection oligonucleotides via the anti-CRISPR/Cas protein primary antibodies and the anti-species secondary antibodies (see complex 9 in Table A and FIG. 6).

The contacting of the cell with the proximity detection probe complex can occur in one step or multiple steps. For example, the cell can be contacted with the first probe and then the cell can be contacted with the second probe at a later time point. Similarly, the cell can be contacted with a first probe comprising a CRISPR/Cas system and then contacted with antibodies directed against the CRISPR/Cas protein and/or antibodies directed against nucleic acid-associated proteins or nucleic acid modifications. In some embodiments, the cell can be contacted with a first probe comprising a CRISPR/Cas system, then contacted with antibodies directed against the CRISPR/Cas protein, and then contacted with secondary anti-species antibodies.

As detailed below, the cell that is contacted with the proximity detection probe complex can be live, fixed, or frozen. In general, the contacting can be performed at a temperature that ranges from about 20° C. to about 40° C.

In some embodiments, a live cell can be contacted with the at least one CRISPR/Cas system-containing probe. The CRISPR/Cas system-containing probes can be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, NUCLEOFECTION® transfection (Lonza Group Ltd.), magnetofection, lipofection, impalefection, optical transfection, proprietary agent-enhanced uptake of nucleic acids, and delivery via liposomes, immunoliposomes, virosomes, or artificial virions. In specific embodiments, the CRISPR/Cas system-containing probes can be introduced into the cell by nucleofection. The CRISPR/Cas system-containing probe can be introduced as a ribonucleoprotein (RNP) complex comprising a recombinant CRISPR/Cas protein (e.g., Cas9 or dCas9) complexed with a guide RNA (e.g., synthesized crRNA and tracrRNA) or the CRISPR/Cas protein and the guide RNA can be introduced into the cell individually. Alternatively, the CRISPR/Cas system can be assembled in the cell after nucleic acid (i.e., mRNA or DNA) encoding the CRISPR/Cas protein and guide RNA are introduced into the cell, or nucleic acid (i.e., mRNA or DNA) encoding the CRISPR/Cas protein and DNA encoding the guide RNA are introduced into the cell. After a suitable period of time, the cell can be fixed (see below) and contacted with (i) antibodies directed against the CRISPR/Cas protein and/or antibodies directed against the nucleic acid-associated protein or nucleic acid modification or (ii) antibodies directed against the CRISPR/Cas protein followed by anti-species secondary antibodies. The cell can be washed with appropriate buffers between any of the contacting steps.

In other embodiments, a fixed cell can be contacted with the at least one CRISPR/Cas system-containing probe. The cell can be fixed using any of a variety of commonly used fixatives. Suitable fixatives include paraformaldehyde, formaldehyde, methanol, acetone, acetic acid, ethanol, glutaraldehyde, iodoform, lactic acid, picric acid, zinc, or combinations thereof. The concentration of fixative and during of the fixation process will vary depending upon the type of cell or sample. In one embodiment, the cell can be fixed with a mixture of methanol and acetic acid (1:1). In another embodiment, the cell can be fixed with 4% paraformaldehyde. In general, the CRISPR/Cas system-containing probe is introduced into the cell as a RNP complex (see above).

In some embodiments, the cell can be permeabilized by incubation with a solution comprising at least one surfactant and/or protease. Non-limiting examples of suitable surfactants include TWEEN® 20, TWEEN® 80, TRITON™ X-100, cetyl alcohol, decyl glucoside, digitonin, lauryl glucoside, IGEPAL CA-630, LEUCOPERM™, NP-40, nonoxynol-9, octaethylene glycol monododecyl ether, n-octyl β-D-thioglucopyranoside, oleyl alcohol, octyl glucoside, Polysorbate 20, Polysorbate 80, saponin, stearyl alcohol, or combinations thereof. Suitable proteases include, without limit, Proteinase K, caspase, chymotrypsin, papain, pepsin, and trypsin. In some embodiments, the cell can be incubated with a solution comprising TWEEN® 20 and/or TRITON™ X-100. The concentration of the surfactant or protease and the duration of the incubation period can and will vary depending upon the type of cell or sample.

In general, the cell is not subjected to a chemical or thermal denaturation process to convert double-stranded chromosomal DNA into single-stranded DNA. In some embodiments, however, the cell can be contacted with a denaturing solution to denature the chromosomal DNA. The denaturing solution can be acidic or alkaline. An acidic solution comprises an acid such as hydrochloric acid, and an alkaline solution comprises a base such as an alkali metal hydroxide (e.g., sodium or potassium hydroxide). The concentration of the acid or base in the denaturing solution and the duration of the denaturation step can and will vary depending upon the type of cell or sample. In other embodiments, the cell can be heated to denature the chromosomal DNA. For example, the cell can be heated to temperature from about 70° C. to about 80° C. in the presence of a formamide containing solution. The duration of the heating step can and will vary depending upon the type of cell or sample.

In embodiments in which the endogenous nucleic acid is RNA, the contacting with the at least one CRISPR/Cas system-containing probe can be conducted in the presence of a PAM-presenting oligonucleotide (i.e., a PAMmer, see O'Connell et al., Nature, 2014, 516:263-266). The PAMmers can be presented in trans to the guide RNA. The PAMmers can comprise standard or modified deoxyribonucleotides, ribonucleotides, or combinations thereof.

After contact with the first and second probes of the proximity detection probe complex, the cell comprises at least one bound proximity detection probe complex.

(b) Visualizing the Bound Proximity Detection Probe Complex

The method further comprises visualizing the bound proximity detection probe complex via an in situ proximity-dependent amplification reaction to detect the endogenous nucleic acid. The in situ proximity-dependent amplification reaction can be a proximity ligation assay (PLA), a proximity-dependent initiation of hybridization chain reaction (proxHCR), or another amplification method that generates an insoluble product or a product that is tethered to the proximity detection probe complex.

PLA.

In embodiments in which the in situ proximity-dependent amplification reaction comprises PLA, the method further comprises contacting the cell with one or more connector oligonucleotides (see, Söderberg, et al., Nature Methods, 2006, 2(12):995-1000). The one or more connector oligonucleotides are generally single-stranded nucleic acids that have sequence complementarity to the first and second proximity detection oligonucleotides of the proximity detection probe complex, and one of the connector oligonucleotides comprises a unique sequence that is not present in the endogenous nucleic acids of the cell. The connector oligonucleotides can comprise standard or modified deoxyribonucleotides, ribonucleotides, or combinations thereof. The connector oligonucleotides can range in length from about 15 nucleotides to about 150 nucleotides. In some embodiments, the connector oligonucleotides can range in length from about 20 nucleotides to about 80 nucleotides. In a specific embodiment, the cell is contacted with two single-stranded connector deoxyoligonucleotides. Upon contact with the connector oligonucleotide(s), the connector oligonucleotide(s) base pair or hybridize with first and second proximity detection oligonucleotides that are in close proximity.

The method further comprises contacting the cell with a ligase, which ligates the hybridized connector oligonucleotide(s) to form a circularized ligation product comprising the unique sequence. The ligase can be T4 DNA ligase, T4 RNA ligase, or App DNA/RNA ligase. The ligase can be mesophilic or thermostable. In a specific embodiment, the ligase is T4 DNA ligase. The ligation reaction is conducted in the presence of a suitable ligase buffer, and at a temperature that ranges from about 20° C. to about 40° C.

The method further comprises amplifying the circularized ligation product comprising the unique sequence by rolling circle amplification to form a rolling circle amplification product comprising repeats of the unique sequence. Thus, the method comprises contacting the cell with a polymerase for rolling circle replication. The polymerase can be phi29 DNA polymerase, bst DNA polymerase, Taq DNA polymerase, T4 DNA polymerase, or T7 DNA polymerase. The polymerase can be mesophilic or thermostable. In specific embodiments, the polymerase is phi29 DNA polymerase. The amplification reaction is conducted in the presence of an amplification solution comprising a suitable polymerase buffer, dNTPs, and other reagents. The amplification reaction is conducted at a temperature that ranges from about 20° C. to about 40° C.

The method further comprises contacting the cell with fluorescently labeled oligonucleotides, which have sequence complementarity to the unique sequence in the connector oligonucleotide. Thus, the labeled oligonucleotides hybridize to the repeated unique sequence within the rolling circle amplification product. The fluorescent label of the labeled oligonucleotide can fluoresce green (e.g., for example, be labeled with Cy2, Alexa 488, or fluorescein and its derivatives such as FAM, HEX, TET, and TRITC), orange (e.g., for example, be labeled with Cy3 or Alexa 546); red (e.g., for example, be labeled with Texas Red, Alexa 594, or rhodamine and its derivatives such as ROX), or far red (e.g., for example, be labeled with Cy5). The labeled oligonucleotides can range in length from about 15 nucleotides to about 30 nucleotides. In specific embodiments, the labeled oligonucleotides can be about 18-22 nucleotides in length. The fluorescently labeled oligonucleotides can be part of the amplification solution described above.

The final step of visualizing the bound proximity detection probe complex comprises detecting the fluorescence of the fluorescently labeled oligonucleotides hybridized to the rolling circle replication product using standard fluorescence microscopy and image analysis software programs. A discrete fluorescent spot indicates the location of the endogenous nucleic acid. The cell can comprise one or more discrete fluorescent spots, depending upon the identity and location of the endogenous nucleic acid of interest.

proxHCR.

In embodiments in which the in situ proximity-dependent amplification reaction comprises proxHCR, the method further comprises contacting the cell with one or more additional oligonucleotides (see, Koos et al., Nature Communications, 2015, 6:7294|DOI:10.1038/ncomms8294). For example, the cell can be contacted with an activator oligonucleotide, at least one 5' fluorescently labeled hairpin oligonucleotide, at least one 3' fluorescently labeled hairpin oligonucleotide, and an initiator oligonucleotide. The activator and hairpin oligonucleotides generally comprise single-stranded regions, as well as stems, loops, hairpin, or other secondary structures. The initiator oligonucleotide is generally single stranded. The oligonucleotides can range in length from about 20 to about 100 nucleotides, and can comprise standard or modified deoxyribonucleotides, ribonucleotides, or combinations thereof. The fluorescent label can be as described above in the PLA section. The fluorescently labeled amplification product can be visualized as detailed above in the PLA section.

(c) Endogenous Nucleic Acids

In some embodiments, the endogenous nucleic acid detected by the method disclosed herein can be nuclear chromosomal DNA. For example, specific chromosomal or genomic loci can be detected in nuclear DNA. The specific chromosomal or genomic locus can be within the coding region of a gene, an intron of a gene, a control region of a gene, a CpG island, a spacer region between genes, a non-coding region, a centromeric region, a telomeric region, a region comprising trinucleotide repeats, and the like. The gene can be a protein coding gene or an RNA coding gene. In some embodiments, the chromosomal or genomic locus can be change or modification, for example a deletion, an insertion, a substitution (e.g., a SNP), a transversion, and the like, in a gene associated with a disease or disorder. In general, the proximity detection probe complex targets two distinct sites in the chromosomal or genomic locus that can be a maximum of about 2 kb apart in cis on the same chromosome.

In other embodiments, the endogenous nucleic acid detected by the method disclosed herein can be a RNA molecule. The RNA molecule can be a messenger RNA (mRNA) or a fragment thereof. The mRNA can be polyadenylated or non-polyadenylated. Alternatively, the RNA molecule can be a non-coding RNA (ncRNA). For example, the ncRNA can be long noncoding RNA (lncRNA), long intergenic non-coding RNA (lincRNA), micro RNA (miRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), telomerase RNA component (TERC), fragments thereof, or combinations thereof.

In still additional embodiments, the endogenous nucleic acid detected by the method disclosed herein can be located in mitochondrial or plastid genomes.

In some embodiments, the method for detecting specific endogenous nucleic acids can be used for research purposes. In other embodiments, the methods for detecting specific endogenous nucleic acids can be used for diagnostic purposes (d) Cells A variety of cells can be used in the method disclosed herein. In general, the cell is an eukaryotic cell. In various aspects, the cell can be a human cell, a non-human mammalian cell, a non-mammalian vertebrate cell, an invertebrate cell, an insect cell, a plant cell, a yeast cell, or a single cell eukaryotic organism. In exemplary aspects, the cell is a mammalian cell. The cell can be a primary cell or a cell line cell. The cell may be an adult cell, an embryonic cell, or a stem cell. The cell can be a normal cell, a diseased cell, or a cancerous cell.

In some embodiments, the cell can be a human cell line cell. Non-limiting examples of suitable cell lines include DU145 (metastatic cancer), SW490 (colon cancer), DLD-1 (colon cancer), KM20L2 (colon cancer), COLO 205 (colon cancer), HCC-2998, (colon cancer), HCT-116 (colon cancer), HCT-15 (colon cancer), HT29 (colon cancer), KM12 (colon cancer), SW-620 (colon cancer), SF-268 (CNS), SF-295 (CNS), SF-539 (CNS), SNB-19 (CNS), SNB-75 (CNS), U251 (CNS), CCRF-CEM (leukemia), HL-60(TB) (leukemia), K-562 (leukemia), MOLT-4 (leukemia), RPMI-8226 (leukemia), SR (leukemia), A549 (non-small cell lung cancer), EKVX (non-small cell lung cancer), HOP-62 (non-small cell lung cancer), HOP-92 (non-small cell lung cancer), NCI-H226 (non-small cell lung cancer), NCI-H23 (non-small cell lung cancer), NCI-H322M (non-small cell lung cancer), NCI-H460 (non-small cell lung cancer), NCI-H522 (non-small cell lung cancer), LOX IMVI (melanoma), MALME-3M (melanoma), M14 (melanoma), MDA-MB-435 (melanoma), SK-MEL-2 (melanoma), SK-MEL-28 (melanoma), SK-MEL-5 U(melanoma), ACC-257(melanoma), UACC-62 (melanoma), IGR-OV1 (ovarian), OVCAR-3 (ovarian), OVCAR-4 OVCAR-5 (ovarian), OVCAR-8 (ovarian), SK-OV-3 (ovarian), 786-0 (renal), A498 (renal), ACHN (renal), CAKI-1 (renal), RXF 393 (renal), SN12C (renal), TK-10 (renal), UO-31 (renal), PC-3 (prostate), DU-145 (prostate), MCF7 (breast), MDA-MB-231 (breast), MDA-MB-468 (breast), HS 578T (breast), BT-549 (breast), and T-47D (breast).

In other embodiments, the cell can be a mammalian cell line cell, Non-limiting examples of suitable mammalian cell lines include Chinese hamster ovary (CHO) cells, baby hamster kidney (BHK) cells; mouse myeloma NS0 cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells; and human embryonic kidney cells (HEK293, HEK293T). An extensive list of mammalian cell lines may be found in the American Type Culture Collection catalog (ATCC, Manassas, Va.).

In still other embodiments, the cell can be within a tissue sample or fluid sample obtained from a subject. For example, a tissue sample or fluid sample can be removed by surgical resection, excisional biopsy, incisional biopsy, core biopsy, or needle aspiration biopsy. The subject can be a human, non-human mammal (e.g., rodent, cat, dog, livestock animal, and the like), or a non-mammalian vertebrate (e.g., fish, birds, and so forth). The tissue sample can be frozen or fixed using a fixative as detailed above. The fixed tissue sample can be embedded in an embedding medium such as paraffin, paraplast, or similar embedding medium known in the art.

III. Kits

A further aspect of the present disclosure entails kits for detecting an endogenous nucleic acid in a cell, wherein a kit comprises at least one probe comprising a CRISPR/Cas system as defined above in section (I)(a).

In some embodiments, the kit comprises (a) a first probe comprising a first CRISPR/Cas system and a first proximity detection oligonucleotide that is linked directly to the CRISPR/Cas protein or the guide RNA of the first CRISPR/Cas system and (b) a second probe comprising a second CRISPR/Cas system and a second proximity detection oligonucleotide that is directly linked to the CRISPR/Cas protein or the guide RNA of the second CRISPR/Cas system.

In other embodiments, the kit comprises (a) a first probe comprising a CRISPR/Cas system and a first proximity detection oligonucleotide that is linked directly to the CRISPR/Cas protein or the guide RNA of the first CRISPR/Cas system and (b) a second probe comprising an antibody directed against a protein associated with the endogenous nucleic acid or an antibody directed against a nucleic acid modification in the endogenous nucleic acid and a second proximity detection oligonucleotide that is linked to the antibody directed against the nucleic acid-associated protein or the antibody directed against the nucleic acid modification.

In other embodiments, the kit comprises (a) a first probe comprising a CRISPR/Cas system and a first proximity detection oligonucleotide that is linked to a primary antibody directed against the CRISPR/Cas protein and (b) a second probe comprising an antibody directed against a protein associated with the endogenous nucleic acid or an antibody directed against a nucleic acid modification in the endogenous nucleic acid and a second proximity detection oligonucleotide that is linked to the antibody directed against the nucleic acid-associated protein or the antibody directed against the nucleic acid modification.

In further embodiments, the kit cell comprises at least one CRISPR/Cas system, first and second proximity detection oligonucleotides linked to anti-species secondary antibodies, and primary antibodies directed against the CRISPR/Cas protein. In some iterations, the kit comprise two CRISPR/Cas systems, three CRISPR/Cas systems, or more than three CRISPR/Cas systems.

The CRISPR/Cas protein of the CRISPR/Cas system can be a Cas9 protein. In some embodiments, the Cas9 protein has nuclease activity, has nickase activity, or is modified to lack all nuclease activity. In specific embodiments, the Cas9 protein comprises at least one nuclear localization signal and is modified to lack all nuclease activity.

In some embodiments, the CRISPR/Cas protein can be provided as a purified protein. In other embodiments, the CRISPR/Cas protein can be provided as encoding nucleic acid (i.e., mRNA or DNA). The nucleic acid encoding the CRISPR/Cas protein can be codon optimized for expression in the cell of interest. The mRNA encoding the CRISPR/Cas protein can be 5' capped and/or 3' polyadenylated. The DNA encoding the CRISPR/Cas protein can be can be operably linked to promoter control sequences (see below), polyadenylation signals (e.g., SV40 polyA signal, bovine growth hormone polyA signal, etc.), and/or transcriptional termination sequences. The DNA encoding the CRISPR/Cas protein can be part of a DNA construct (e.g., plasmid vector, lentiviral vector, adeno-associated viral vector, phagemid, cosmid, artificial/mini-chromosome, and so forth). In some embodiments, the DNA can be operably linked to a promoter control sequence for expression in a cell of interest. Suitable mammalian promoter control sequences include the cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, and the like. In other embodiments, the DNA can be operably linked to a promoter control sequence that is recognized by a phage RNA polymerase for in vitro mRNA synthesis. For example, the promoter sequence can be a T7, T3, or SP6 promoter sequence or a variation of a T7, T3, or SP6 promoter sequence. In further embodiments, the DNA can be operably linked to a promoter sequence for in vitro expression in bacterial or eukaryotic cells. Suitable bacterial promoters include, without limit, T7 promoters, lac operon promoters, trp promoters, tac promoters (which are hybrids of trp and lac promoters), variations thereof any of the foregoing, and combinations thereof of any of the foregoing. Non-limiting examples of suitable eukaryotic promoters are well known in the art and include the mammalian promoter sequences listed above.

In certain embodiments, the kit can further comprise at least one vector system for in vitro transcription of one or more guide RNAs. For example, the vector system can comprise a promoter sequence that is recognized by a phage RNA polymerase for in vitro RNA synthesis. The phage promoter sequence can be a T7, T3, or SP6 promoter or variant thereof. In other embodiments, the kit can comprise at least one vector system for in vivo expression of one or more guide RNAs. DNA encoding the guide RNA(s) can be operably linked to a promoter sequence that is recognized by RNA polymerase III (Pol III). Examples of suitable Pol III promoters include, but are not limited to, mammalian U6, U3, H1, and 7SL RNA promoters. The vector system can further comprise a polylinker region containing multiple cloning sites for insertion of DNA encoding the guide RNA of interest. The vector system can further comprise an origin or replication, a selection marker gene, and/or amplification or sequencing primer sites.

In still other embodiments, the kit can further comprise at least one reagent for an in situ proximity-dependent amplification reaction. In some embodiments, the kit can comprise at least one reagent for PLA. The PLA reagent can be one or more connector oligonucleotides, a ligase, a ligation reagent, a polymerase, an amplification reagent, a fluorescently labeled detection oligonucleotide, or combinations thereof. In other embodiments, the kit can comprise activator, labeled detector, and/or initiator oligonucleotides for proxHCR.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are complementary.

As used herein, the term "endogenous" refers to a nucleic acid that is native to the cell.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

The following example illustrates certain aspects of the invention.

Example 1: Detecting Centromeres Using dCas9-gRNA Complexes

Figure 7:
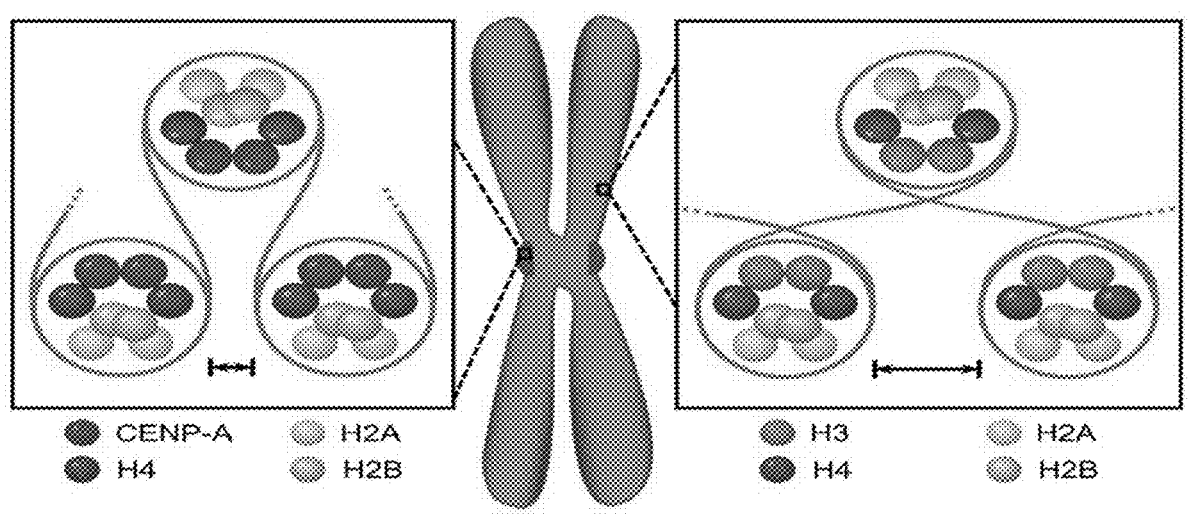
FIG. 7 presents a schematic diagram of a chromosome. Centromeric chromatin is unique because CENP-A (left) replaces histone H3 (right).

Centromeric satellite DNA comprises large arrays of tandemly repeating, non-coding sequences, and centromeric chromatin is unique in that histone H3 is replaced with CENP-A (see FIG. 7). To determine whether centromeres could be detected using the methods disclosed herein, a probe comprising a Cas9 system targeted to minor satellite repeat sequence or major satellite repeat sequence was constructed to use in combination with a proximity ligation assay (PLA) (e.g., DUOLINK® assay) and antibodies to CENP-A.

The CRISPR/Cas probe was formed as ribonucleoprotein (RNP) complexes by combining recombinant dCas9 (i.e., D10A/H840A double mutant; 1 pmol) with synthesized DIG-tracrRNA (2 pmol) and crRNAs (2 pmol) which targeted either the minor satellite repeat sequence, major satellite repeat sequence, or a negative control 1 sequence (that does not target any known human sequence). DIG-tracrRNA and crRNA sequences used were as indicated in Table 1. U2OS cells were nucleofected with the RNPs using standard reagents and equipment. Nucleofected cells were diluted 1:10 in complete medium (DMEM+10% FBS without antibiotics) and seeded onto 8-well chambered cover-glass slides. For all subsequent steps in the procedure, 40 µl reagent/well was used. After 6 hours, the cells were fixed with 4% para-formaldehyde for 15 minutes at RT, quenched with $\frac{1}{10}^{th}$ volume 1.25M Glycine for 5 minutes at RT, washed with PBS and permeabilized for 1 hour in permeabilization buffer (0.75% TRITON™ X-100, 0.75% TWEEN® 20) and blocked with PLA blocking buffer for 1 hour at RT.

TABLE 1 crRNA and tracrRNA sequences.

| | Sequence | SEQ ID NO: |
|---|---|---|
| sgMajor Satellite | 5'-CCAUAUUCCACGUCCUACAGUGUUUU AGAGCUAUGCUGUUUUG-3' | 9 |
| sgMinor Satellite | 5'-AUCUAAUAUGUUCUACAGUGUGUUUA GAGCUAUGCUGUUUUG-3' | 10 |
| Negative control 1 | 5'-CGCGAUAGCGCGAAUAUAUUGUUUUAG AGCUAUGCUGUUUUG-3' | 11 |
| tracrRNA | 5'-DIG-AAACAGCAUAGCAAGUUAAAAUAA GGCUAGUCCGUUAUCAACUUGAAAAAGUGG CACCGAGUCGGUGCU-3' | 12 |

The PLA assay was performed with anti-Cas9 antibodies (mouse, Diagenode, 1:3000 dilution) and anti-CENP-A antibodies (rabbit, Cell Signalling, 1:1000 dilution), which were incubated overnight at 4° C. Cells were washed with PLA wash buffer A (2×5 minutes). Diluted PLA secondary Ab-PLA probe solutions [anti-Rabbit (+) and anti-Mouse (−)] (1:5 dilution) were added and the slides were incubated in a pre-heated humidity chamber for 1 hour at 37° C. The cells were washed with PLA wash Buffer A (2×5 min, RT) with gentle orbital shaking. The ligation reaction was performed, the cells were washed, and the amplification reaction was performed (Far red kit) essentially as described in the PLA (DUOLINK® Fluorescent) user guide. Cells were stained with DAPI (for DNA) and Phalloidin-Atto488 (for actin), washed and flooded with PBS, covered with a glass slide, corners were sealed with clear nail polish hardener and observed in a fluorescent microscope.

Figure 8A:
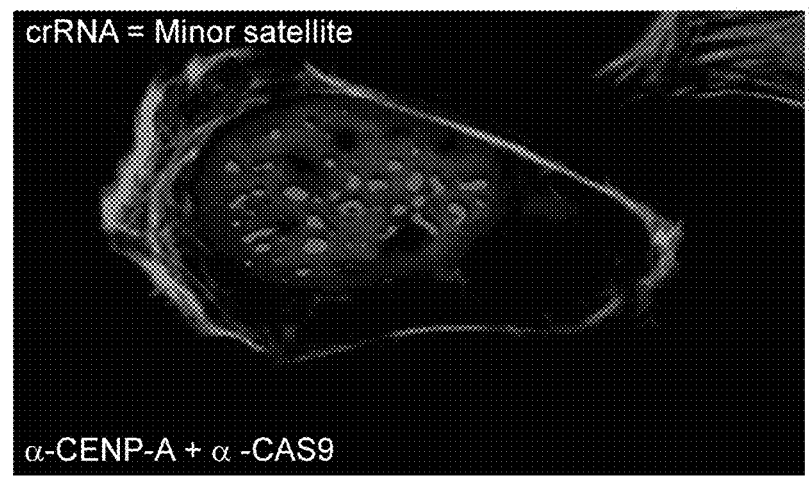
FIGS. 8A-D show images of U2OS cells nucleofected with CRISPR RNP complexes formed with dCas9, DIG-tracrRNA, and either minor satellite crRNA or negative control 1 (NC1) crRNA. PLA (DUOLINK®) assay was performed using anti-Cas9 and/or anti-CENP-A antibodies. Overlaid images show Duolink signal (Cy5), nucleus (DNA) (DAP), and actin (Phalloidin Atto488).
Figure 8B:
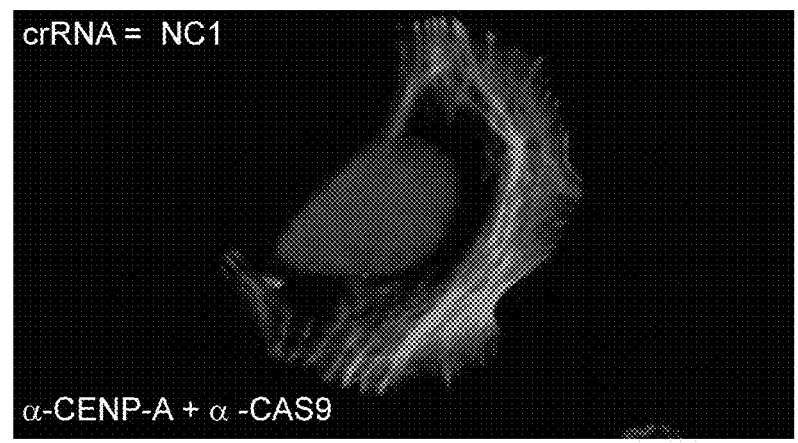
Figure 8C:
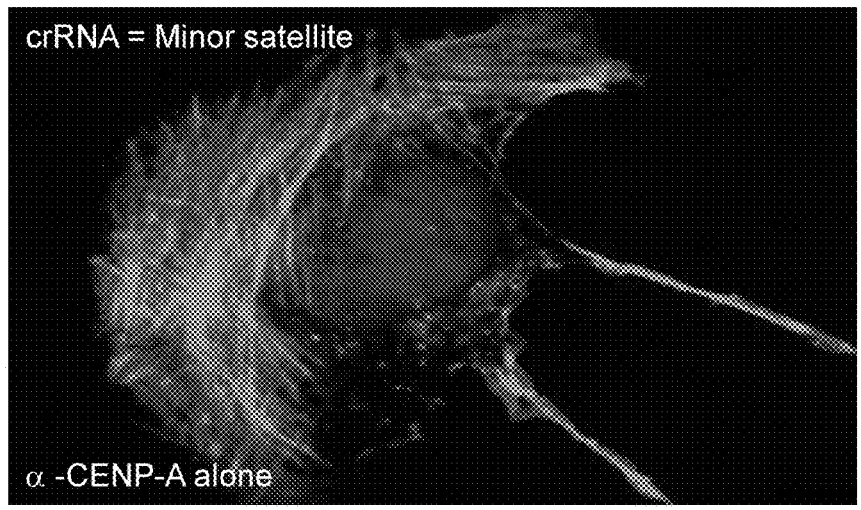
Figure 8D:
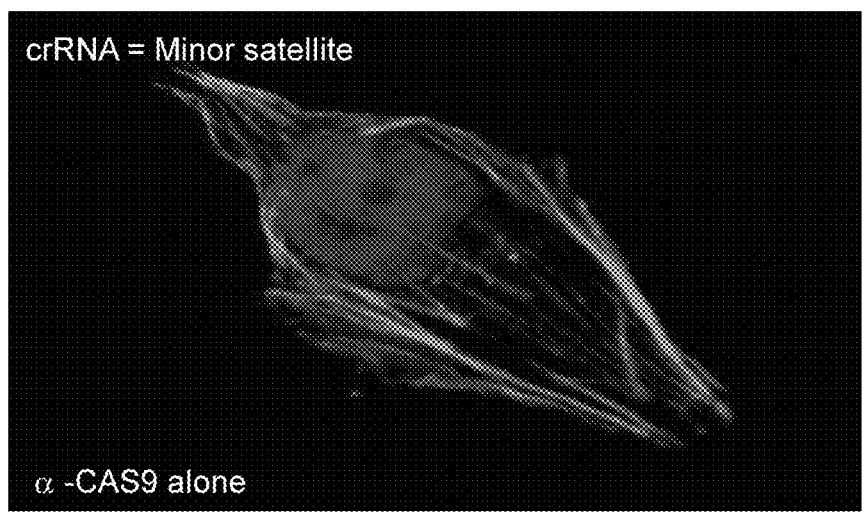

Centromeres were visualized as red punctate dots only when crRNAs targeting the minor satellite repeats were used to form the CRISPR RNPs (FIG. 8A) but not when negative control (NC1) crRNAs were used (FIG. 8B) or major satellite crRNAs were used (data not shown). PLA amplification was triggered using both anti-Cas9 and anti- CENP-A antibodies (FIG. 8A). Using either anti-CENP-A antibodies alone (FIG. 8C) or anti-Cas9 antibodies alone (FIG. 8D) did not give a PLA (DUOLINK®) signal, indicating the dual specificity and proximity dependent nature of PLA amplification.

Example 2: Detecting Telomeres Using dCas9-gRNA Complexes

Figure 9A:
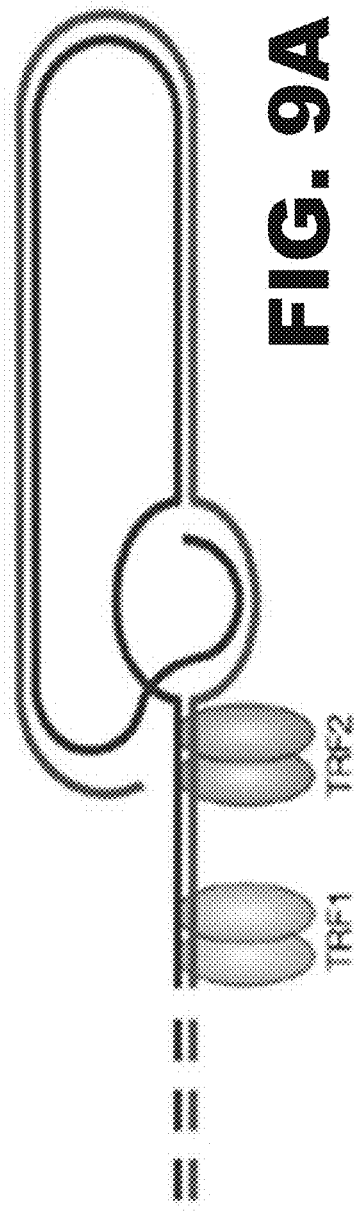
FIG. 9A schematically illustrates a telomere with associated TRF1 and TRF2 proteins.
Figure 9B:
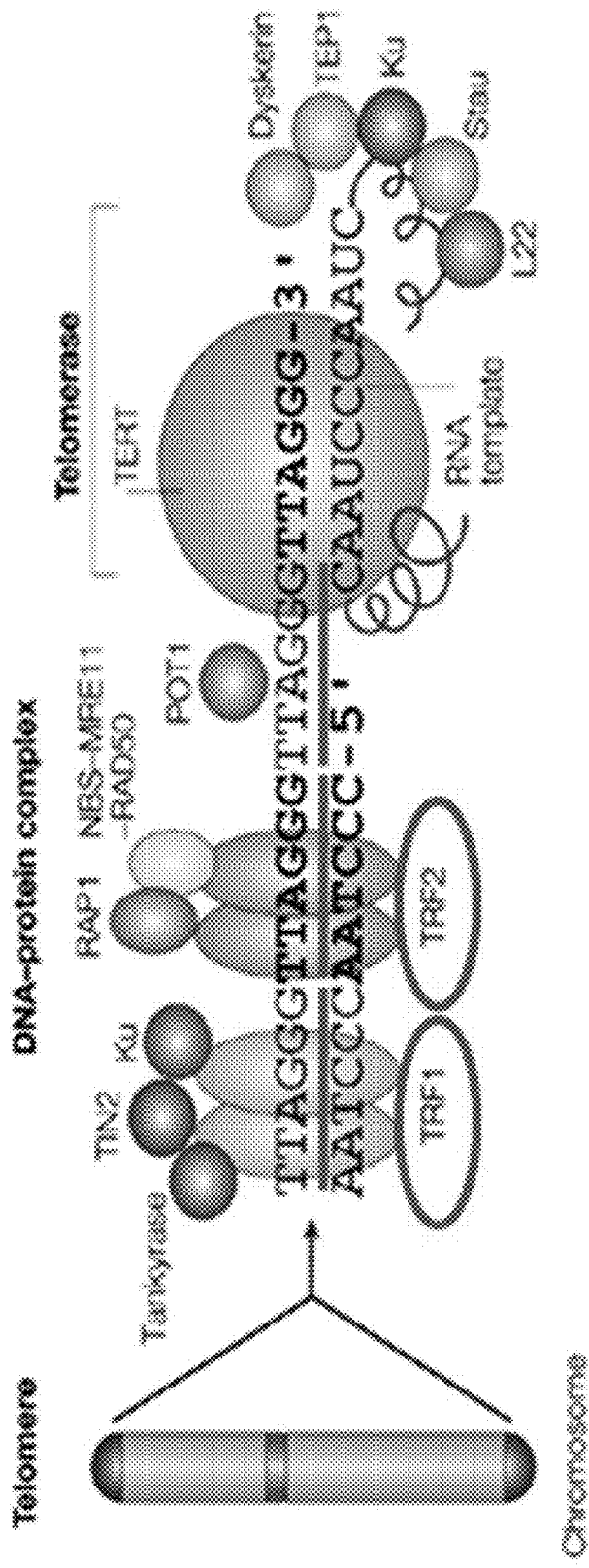
FIG. 9B illustrates the binding of TRF1 and TRF2 proteins to the telomere repeat sequence TTAGGG (underlined) of telomere DNA (5'-TTAGGGTTAGGGTTAGGGTTAGGG-3'; SEQ ID NO:18), which is base paired with DNA (AATCC-CAATCCC; SEQ ID NO:19) or telomerase template RNA comprising CAAUCCCAAUC (SEQ ID NO:20).

TRF1 and TRF2 are proteins associated with telomere repeats at the ends of chromosomes (see FIGS. 9A, B). TRF2 and TRF1 bind to the telomere repeat sequence 5'-TTAGGG-3'. Telomeres were detected in U2OS cells using a procedure similar to that described above in Example 1 with the following changes. (a) RNP complexes s were assembled with crRNA (5'-UAGGGUUAGG-GUUAGGGUUAUGUUUUAGAGCUAUGCU-GUUUUG-3; SEQ ID NO:13) targeting the telomere repeat sequence, and (b) the PLA assay was performed with anti-Cas9 antibodies (mouse, Diagenode, 1:3000 dilution) and anti-TRF2 antibodies (Rabbit, Cell Signalling, 1:1000 dilution) antibodies (overnight at 4° C.).

Figure 10A:
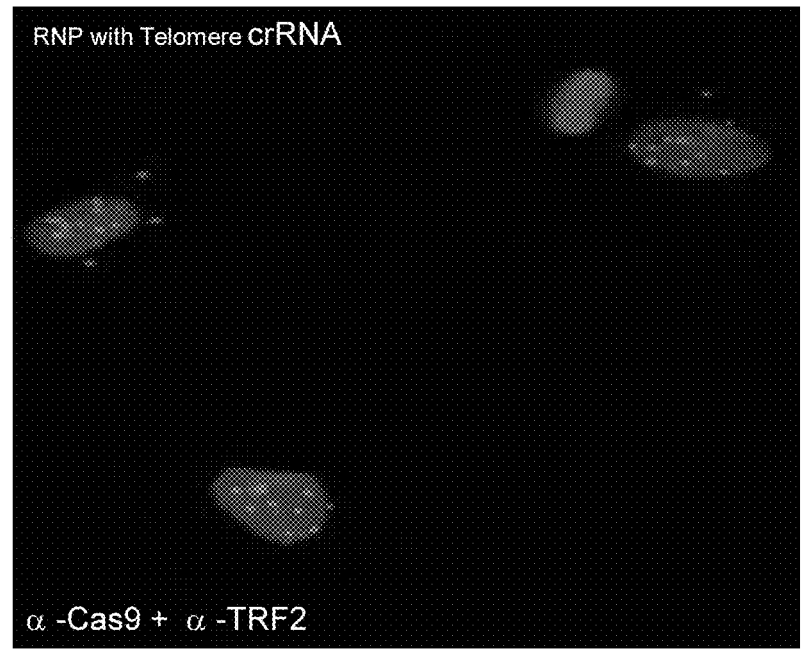
FIGS. 10A-D show images of U2OS cells nucleofected with CRISPR RNP complexes formed with dCas9, DIG-tracrRNA, and either telomere crRNA or negative control 1 (NC1) crRNA. PLA (DUOLINK®) assay was performed using anti-Cas9 and/or anti-TRF2 antibodies. Overlaid images show Duolink signal (Cy5) and nucleus (DNA) (DAPI).
Figure 10B:
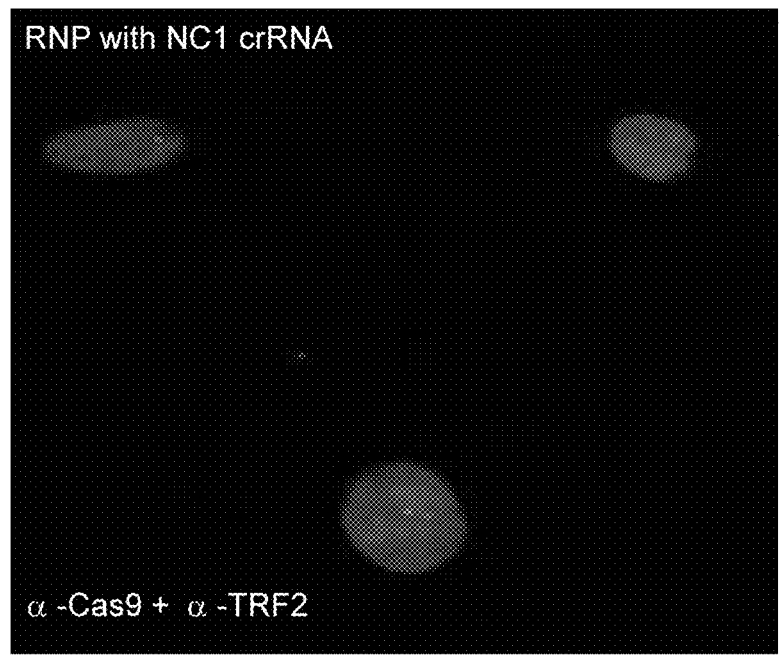
Figure 10C:
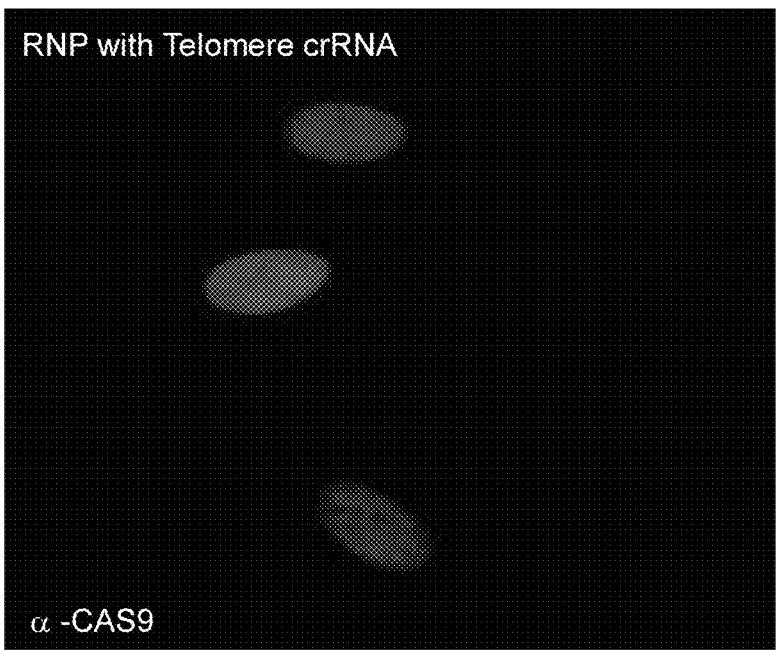
Figure 10D:
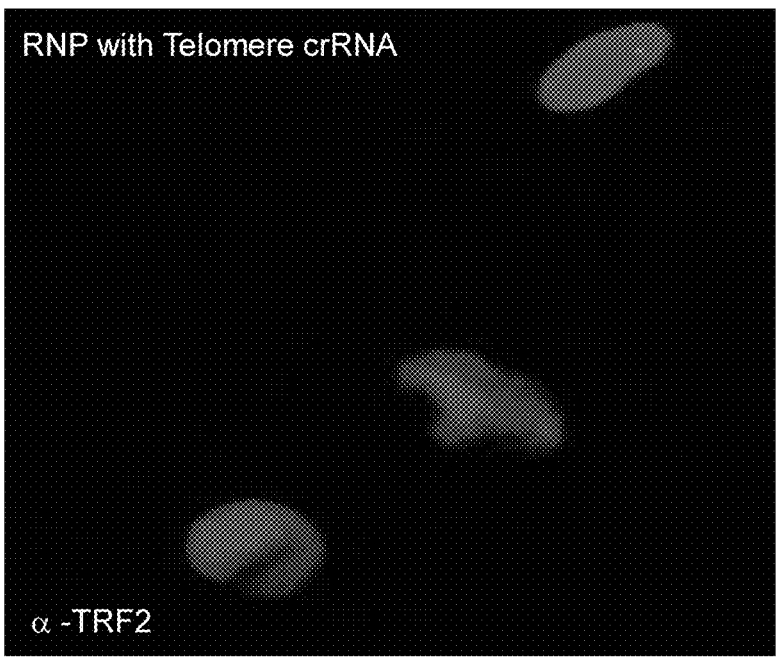

Telomeres were visualized as red punctate dots only when crRNAs targeting the telomere repeat sequence were used to form the CRISPR RNPs (FIG. 10A) but not when negative control 1 (NC1) crRNAs were used (FIG. 10B). PLA amplification was triggered when both anti-Cas9 and anti-TRF2 antibodies were used (FIG. 10A). Using either anti-Cas9 antibodies alone (FIG. 10C) or anti-TRF2 antibodies alone (FIG. 10D) did not give a PLA (DUOLINK®) signal, indicating the dual specificity and proximity dependent nature of PLA amplification.

Example 3: Detecting Centromeres in Fixed Cells Using dCas9-gRNA Complexes

U2OS cells were fixed with 1% paraformaldehyde for 10 minutes at RT, quenched with $1/10^{th}$ volume 1.25 M glycine for 5 minutes at RT, washed with PBS. Cells were then permeabilized for 1 hour in permeabilization buffer (0.75% TRITON™ X-100, 0.75% TWEEN® 20) and blocked with PLA blocking buffer for 1 hour at RT. CRISPR was formed as ribonucleoprotein (RNP) complexes by combining recombinant dCas9 (1 pmol) with synthesized DIG-tracrRNA (2 pmol) which target either the minor satellite repeat sequence, major satellite repeat sequence or the negative control 1 sequence (that does not target any known human sequence). DIG-tracrRNA and crRNA sequences are indicated in Table 1. After blocking, the cells were washed with PBS. Cells were covered by PBS (30 µL) and the slides were sealed with hybridization covers (HYBRISLIP™; GraceBioLabs) and chromosomal DNA was denatured by incubating the slide (with the cells) at 80° C. for 5 minutes. PBS was aspirated and RNPs (diluted 1:10 with Cas9 buffer: 20 mM HEPES pH 7.5, 150 mM KCl, 1% sucrose) were added, the slides were sealed with hybridization covers and incubated overnight (16 hrs) at 37° C. in a slide hybridizer (THERMOBRITE®; Leica Biosystems). Cells were washed with PLA wash buffer A (2×5 minutes each in cover jar) before proceeding with the PLA (DUOLINK®) assay essentially as described above in Example 1.

Figure 11A:
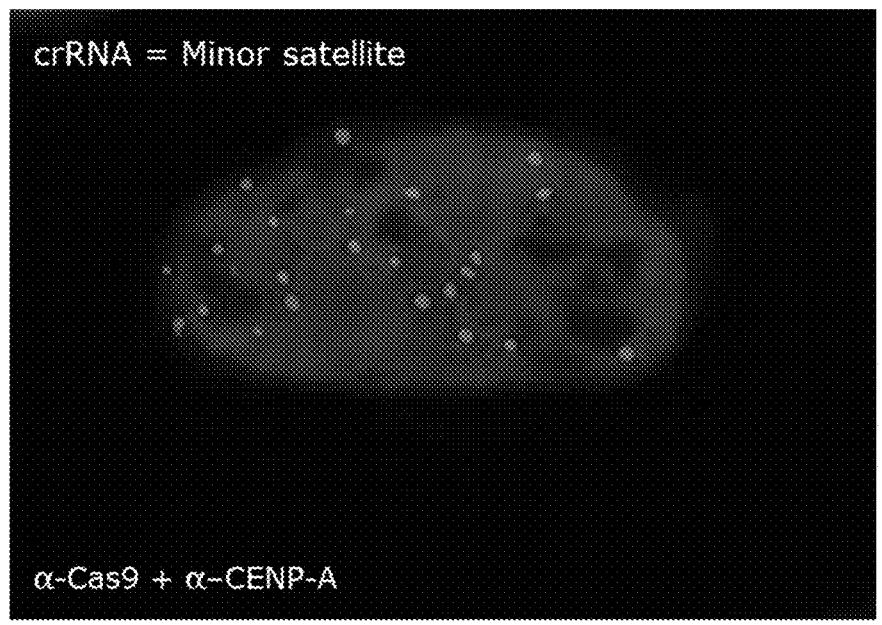
FIGS. 11A-D show images of fixed U2OS cells incubated with CRISPR RNP complexes formed with dCas9, DIG-tracrRNA, and either minor satellite crRNA or negative control 1 (NC1) crRNA. PLA (DUOLINK®) assay was performed using anti-Cas9 and/or antiCENP-A antibodies. Overlaid images show Duolink signal (Cy5) and nucleus (DNA) (DAPI).
Figure 11B:
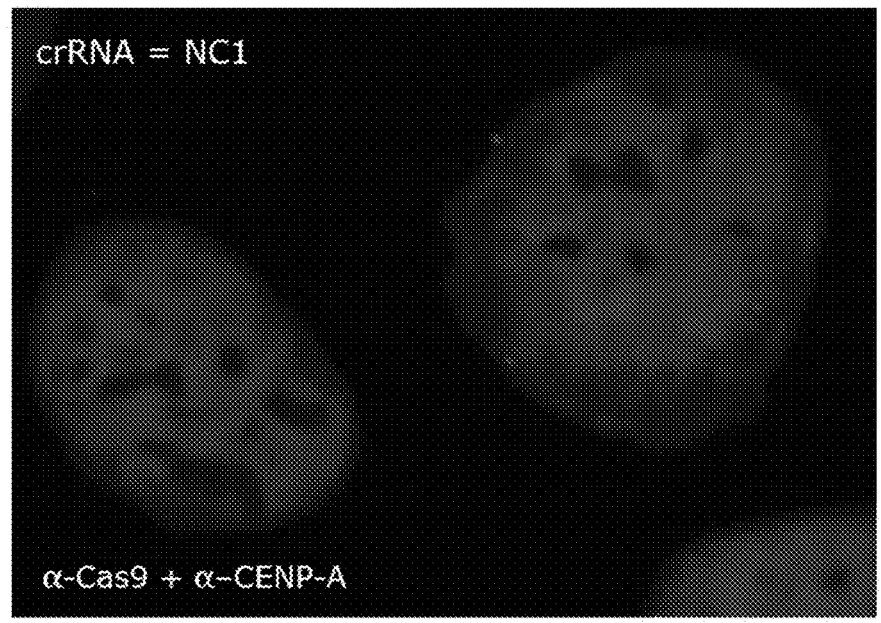
Figure 11C:
Figure 11D:
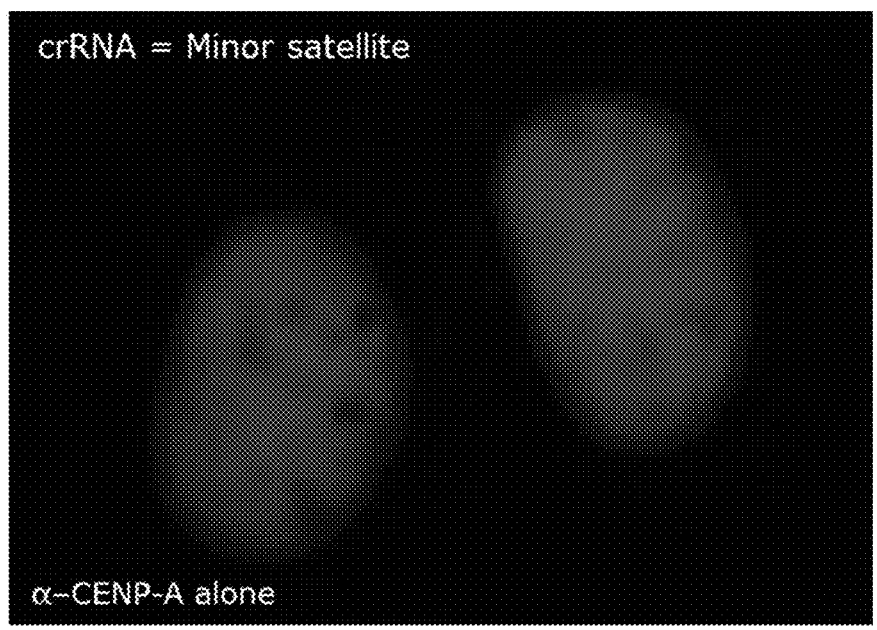

Centromeres were visualized as red punctate dots only when crRNAs targeting the minor satellite repeats were used to form the CRISPR RNPs (FIG. 11A) but not when negative control (NC1) crRNAs were used (FIG. 11B) or major satellite crRNAs were used (data not shown). PLA amplification was triggered using both anti-Cas9 and anti-CENP-A antibodies (FIG. 11A). Using either anti-Cas9 antibodies alone (FIG. 11C) or anti-CENP-A antibodies alone (FIG. 11D) did not give a PLA (DUOLINK®) signal, indicating the dual specificity and proximity dependent nature of PLA amplification.

Example 4: Detecting a Genomic Locus Using dCas9-gRNA Complexes

Purified recombinant dCas9 (i.e., D10A/H840A double mutant) can be complexed with crRNA or crRNA pools (that tile to target a specific genomic locus) and tracrRNA to form dCas9-gRNA complexes to use to recognize genomic loci. For example, one or more gRNAs can be designed within a 2 kb region surrounding targets sites in AAVS1, EMX1, or Kras (i.e., 1 kb upstream and 1 kb downstream). The human gRNA targets (and non-target) are shown below.

```
1. AAVS1-gRNA
(Target site: GGGCCACTAGGGACAGGATTG

G; SEQ ID NO: 14)

2. EMX1-gRNA
(Target site: AGTCCGAGCAGAAGAAGA

A; SEQ ID NO: 15)

3. Kras-gRNA
(Target site: TAGTTGGAGCTGGTGGCG

T; SEQ ID NO: 16)

4. Non-target
(Target site: CGCGATAGCGCGAATATAT

T; SEQ ID NO: 17)
```

The dCas9-gRNA complexes can be added to live or fixed cells essentially as described above in Examples 1-3, and the localized complexes can be detected using a PLA assay. For this, the cells can be incubated anti-Cas9 antibodies (rabbit), then incubated with anti-rabbit PLA probes with (+) and (−) oligos followed by the connector oligos (that will bridge the (+) and (−) oligos and have an internal non-mammalian repeat sequence). Next, a ligation reaction will form the circular DNA template(s) wherever the (+) and (−) probes are located within about 40 nm proximity. These circular DNA molecules will serve as templates for rolling circle amplification using phi29 DNA polymerase. Localized amplified DNA can be visualized using fluorescent (e.g., far red) oligo probes that will hybridize specifically to the non-mammalian repeat sequence of the amplified template. Punctate bright red signals observed using a fluorescent microscope with the Cy5 filter indicate a PLA signal.

What is claimed is:

1. A complex comprising at least one probe comprising (i) an engineered, non-naturally occurring Clustered Regularly Interspersed Short Palindromic Repeats (CRISPR)-associated (Cas) (CRISPR/Cas) system comprising a Cas9 protein and a guide RNA and (ii) an oligonucleotide that is linked directly or indirectly to the CRISPR/Cas system, wherein the guide RNA comprises the nucleotide sequence of SEQ ID NO:9.

2. The complex of claim 1, wherein the Cas9 protein comprises two functional nuclease domains, one functional nuclease domain, or no functional nuclease domains.

3. The complex of claim 1, wherein the complex comprises a first probe comprising (i) the CRISPR/Cas system and (ii) a first oligonucleotide that is linked to the guide RNA by covalent or non-covalent bonds.

* * * * *

SEQUENCE LISTING

<160> NUMBER OF SEQ ID NOS: 20

<210> SEQ ID NO 1

```
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 1

Pro Lys Lys Lys Arg Lys Val
1               5

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Pro Lys Lys Lys Arg Arg Val
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 4

Gly Arg Lys Lys Arg Arg Gln Arg Arg Arg Pro Pro Gln Pro Lys Lys
1               5                   10                  15

Lys Arg Lys Val
            20

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 5

Pro Leu Ser Ser Ile Phe Ser Arg Ile Gly Asp Pro Pro Lys Lys Lys
1               5                   10                  15

Arg Lys Val

<210> SEQ ID NO 6
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 6

Gly Ala Leu Phe Leu Gly Trp Leu Gly Ala Ala Gly Ser Thr Met Gly
```

```
1               5                   10                  15
Ala Pro Lys Lys Lys Arg Lys Val
            20
```

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 7

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 8
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 8

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 9
<211> LENGTH: 43
<212> TYPE: RNA
<213> ORGANISM: Artificial Sequence
<220> FEATURE:
<223> OTHER INFORMATION: SYNTHESIZED

<400> SEQUENCE: 9
ccauauucca cguccuacag uguuuuagag cuaugcuguu uug                            43

<210> SEQ ID NO 10
<211> LENGTH: 43
<212> TYPE: RNA
<213> ORGANISM: Artificial Sequence
<220> FEATURE:
<223> OTHER INFORMATION: SYNTHESIZED

<400> SEQUENCE: 10
aucuaauaug uucuacagug uguuuuagag cuaugcuguu uug                            43

<210> SEQ ID NO 11
<211> LENGTH: 42
<212> TYPE: RNA
<213> ORGANISM: Artificial Sequence
<220> FEATURE:
<223> OTHER INFORMATION: SYNTHESIZED

<400> SEQUENCE: 11
cgcgauagcg cgaauauauu guuuuagagc uaugcuguuu ug                             42

<210> SEQ ID NO 12
<211> LENGTH: 69
<212> TYPE: RNA
<213> ORGANISM: Artificial Sequence
<220> FEATURE:

```
<223> OTHER INFORMATION: SYNTHESIZED

<400> SEQUENCE: 12
aaacagcaua gcaaguuaaa auaaggcuag uccguuauca acuugaaaaa guggcaccga    60
gucggugcu                                                           69

<210> SEQ ID NO 13
<211> LENGTH: 43
<212> TYPE: RNA
<213> ORGANISM: Artificial Sequence
<220> FEATURE:
<223> OTHER INFORMATION: SYNTHESIZED

<400> SEQUENCE: 13
uaggguuagg guuagggutua uguuuuagag cuaugcuguu uug                    43

<210> SEQ ID NO 14
<211> LENGTH: 22
<212> TYPE: DNA
<213> ORGANISM: Homo sapiens

<400> SEQUENCE: 14
gggccactag ggacaggatt gg                                            22

<210> SEQ ID NO 15
<211> LENGTH: 19
<212> TYPE: DNA
<213> ORGANISM: Homo sapiens

<400> SEQUENCE: 15
agtccgagca gaagaagaa                                                19

<210> SEQ ID NO 16
<211> LENGTH: 19
<212> TYPE: DNA
<213> ORGANISM: Homo sapiens

<400> SEQUENCE: 16
tagttggagc tggtggcgt                                                19

<210> SEQ ID NO 17
<211> LENGTH: 20
<212> TYPE: DNA
<213> ORGANISM: Homo sapiens

<400> SEQUENCE: 17
cgcgatagcg cgaatatatt                                               20

<210> SEQ ID NO 18
<211> LENGTH: 24
<212> TYPE: DNA
<213> ORGANISM: Homo sapiens

<400> SEQUENCE: 18
ttagggttag ggttagggtt aggg                                          24

<210> SEQ ID NO 19
<211> LENGTH: 12
<212> TYPE: DNA
<213> ORGANISM: Homo sapiens

<400> SEQUENCE: 19
aatcccaatc cc                                                       12
```

```
<210> SEQ ID NO 20
<211> LENGTH: 11
<212> TYPE: RNA
<213> ORGANISM: Homo sapiens

<400> SEQUENCE: 20
caaucccaau c                                                          11
```